United States Patent [19]

Das et al.

[11] Patent Number: 4,752,645
[45] Date of Patent: Jun. 21, 1988

[54] BENZAZEPINE DERIVATIVES

[75] Inventors: Jagabandhu Das, Hamilton Square; David Floyd, Pennington; John Krapcho, Somerset, all of N.J.

[73] Assignee: E. R. Squibb & Sons, Inc., Princeton, N.J.

[21] Appl. No.: 52,300

[22] Filed: May 21, 1987

Related U.S. Application Data

[63] Continuation-in-part of Ser. No. 917,130, Oct. 9, 1986, abandoned, which is a continuation-in-part of Ser. No. 808,183, Dec. 12, 1985, abandoned.

[51] Int. Cl.$^4$ .................. C07D 223/16; A61K 31/55
[52] U.S. Cl. ...................................................... 540/523
[58] Field of Search ........................................ 540/523

[56] References Cited

U.S. PATENT DOCUMENTS

| | | | |
|---|---|---|---|
| 3,075,967 | 1/1963 | Krapcho | 540/491 |
| 3,312,691 | 4/1967 | Werner | 540/523 |
| 3,330,823 | 7/1967 | Bernstein et al. | 540/523 |
| 3,562,257 | 2/1971 | Kugita et al. | 540/491 |
| 3,748,321 | 7/1973 | Krapcho | 540/523 |

OTHER PUBLICATIONS

The Merck Index, ninth edition, 1976, p. 425, Abstract No. 31187, Diltiazam.
Chem. Pharm. Bull., vol. 33, pp. 634-641, Hasiyama et al.
J. Cardiovasc. Pharm., vol. 7, p. 152 (1985), Yabana et al.
J. Cardiovasc. Pharm., vol. 9, p. 173 (1987), Schoemaker et al.

Primary Examiner—Robert T. Bond
Attorney, Agent, or Firm—Lawrence S. Levinson; Donald J. Barrack

[57] ABSTRACT

Vasodilating activity is exhibited by compounds having the formula

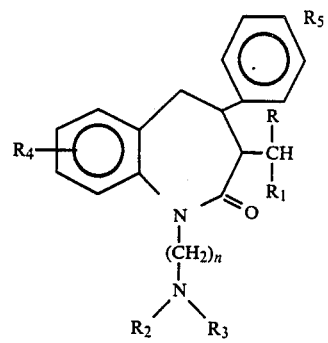

and pharmaceutically acceptable salts thereof.

40 Claims, No Drawings

BENZAZEPINE DERIVATIVES

This application is a continuation-in-part of U.S. patent application Ser. No. 917,130, filed Oct. 9, 1986, and now abandoned which is a continuation-in-part of U.S. patent application Ser. No. 808,183, filed Dec. 12, 1985, and now abandoned.

BRIEF DESCRIPTION OF THE INVENTION

Compounds having the formula

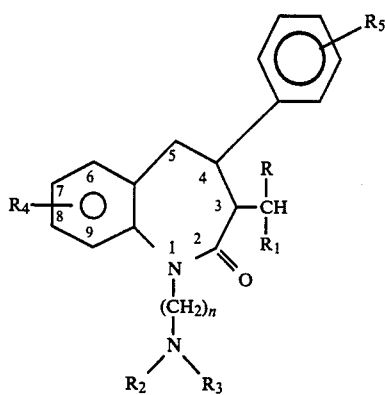

and the pharmaceutically acceptable salts thereof, have useful vasodilating activity. In formula I, and throughout the specification, the symbols are as defined below.

R and $R_1$ are each hydrogen or alkyl, R is hydrogen and $R_1$ is alkyl, alkenyl, alkynyl, aryl, heteroaryl or cycloalkyl, or R and $R_1$ together with the carbon atom to which they are attached ar cycloalkyl;

$R_2$ and $R_3$ are each independently hydrogen, alkyl, cycloalkyl, or arylalkyl or $R_2$ and $R_3$ together with the nitrogen atom to which they are attached are pyrrolidinyl, piperidinyl, or morpholinyl;

$R_4$ and $R_5$ are each independently hydrogen, halogen, alkyl, alkoxy, aryloxy, arylalkoxy, arylalkyl, hydroxy, alkanoyloxy,;

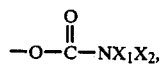

difluoromethoxy, trifluoromethyl, $-NX_3X_4$, $-S(O)_m$alkyl, or $-S(O)_m$aryl;

n is 2 or 3;

m is 0, 1 or 2;

$X_1$ and $X_2$ are each independently hydrogen, alkyl, aryl or heteroaryl, or $X_1$ and $X_2$ together with the nitrogen atom to which they are attached are a nitrogen containing heteroaryl;

$X_3$ and $X_4$ are each independently hydrogen, alkyl, alkanoyl, arylcarbonyl, heteroarylcarbonyl, carbamoyl

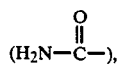

alkylsulfonyl or arylsulfonyl; with the proviso that if $R_4$ is a 7-alkyl group, it must have a tertiary carbon atom bonded to the ring.

Listed below are definitions of various terms used to describe the benzazepines of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The term "aryl" refers to phenyl and substituted phenyl. Exemplary substituted phenyl groups are phenyl groups substituted with 1, 2 or 3 amino ($-NH_2$), alkylamino, dialkylamino, nitro, halogen, hydroxyl, trifluoromethyl, alkyl (of 1 to 4 carbon atoms), alkoxy (of 1 to 4 carbon atoms), alkanoyloxy, carbamoyl, or carboxyl groups.

The term "alkanoyl" refers to groups having the formula

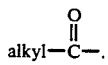

Those alkanoyl groups are preferred.

The term "heteroaryl" refers to an aromatic heterocyclic group having at least one heteroatom in the ring. Preferred groups are pyridinyl, pyrrolyl, imidazolyl, furyl, thienyl, or thiazolyl.

The term "nitrogen containing heteroaryl" refers to an aromatic heterocyclic group having at least one nitrogen atom in the ring. Preferred groups are pyridinyl, pyrrolyl, imidazolyl and thiazolyl.

The term "cycloalkyl" refers to groups having 3, 4, 5, 6 or 7 carbon atoms.

The terms "halogen" refers to fluorine, chlorine, bromine and iodine.

The terms "alkenyl" and "alkynyl" refer to both straight and branched chain groups. Those groups having 2 to 10 carbon atoms are preferred.

The compounds of formula I form acid-addition salts with inorganic and organic acids. These acid-addition salts frequently provide useful means for isolating the products from reaction mixtures by forming the salt in a medium in which it is insoluble. The free base may then be obtained by neutralization, e.g., with a base such as sodium hydroxide. Any other salt may then be formed from the free base and the appropriate inorganic or organic acid. Illustrative are the hydrohalides, especially the hydrochloride and hydrobromide, sulfate, nitrate, phosphate, borate, acetate, tartrate, maleate, citrate, succinate, benzoate, ascorbate, salicylate, methanesulfonate, benzenesulfonate, toluenesulfonate and the like.

The carbon atoms in the 3 and 4-positions of the benzazepine nucleus of the compound of formula I are asymmetric carbons. The compounds of formula I, therefore, exist in enantiomeric and diastereomeric forms and as racemic mixtures thereof. All are within the scope of this invention. It is believed that those compounds of formula I which have the d-cis configuration are the most potent and are therefore preferred.

DETAILED DESCRIPTION OF THE INVENTION

The compounds of formula I and the pharmaceutically acceptable salts thereof are useful as cardiovascular agents. These compounds act as vasodilators and are especially useful as anti-hypertensive agents. By the administration of a composition containing one (or a combination) of the compounds of this invention the blood pressure of a hypertensive mammalian (e.g., human) host is reduced. Daily doses of about 0.1 to 100 mg. per kilogram of body weight per day, preferably about 1 to about 50 mg. per kilogram per day, are appropriate to reduce blood pressure, and can be administered in single or divided doses. The substance is preferably administered orally, but parenteral routes such as the subcutaneous, intramuscular, or intravenous routes can also be employed.

As a result of the vasodilating activity of the compounds of formula I, it is believed that such compounds in addition to being anti-hypertensives may also be useful as anti-arrhythmic agents, as anti-anginal agents, as anti-fibrillatory agents, as anti-asthmatic agents, and in limiting myocardial infarction.

The compounds of this invention can also be formulated in combination with a diuretic, or a beta-adrenergic agent, or angiotensin converting enzyme inhibitor. Suitable diuretics include the thiazide diuretics such as hydrochlorothiazide and bendroflumethiazide, suitable beta-adrenergic agents include nadolol, and suitable angiotensin converting enzyme inhitibors include captopril.

The compounds of formula I can be prepared by first reacting a 2-nitrotoluene having the formula

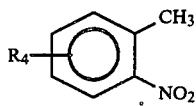

with a benzylidene malonate having the formula

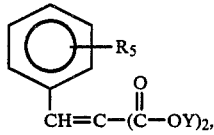

wherein Y is alkyl. The reaction can be run in a polar nonprotic solvent (e.g., dimethylformamide), in the presence of a strong base such as sodium hydride, and yields a product having the formula

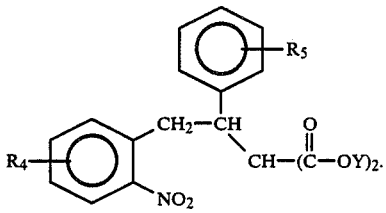

Reduction of a compound of formula IV yields the corresponding compound having the formula

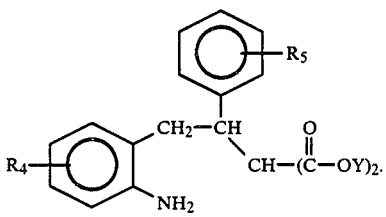

The reduction can be accomplished by catalytic hydrogenation (using, for example, palladium on charcoal as a catalyst) or using a chemical reducing agent (e.g., ferrous sulfate or stannous chloride).

Treatment of an amine of formula V with an alkali metal alkoxide (e.g., sodium methoxide) and an alcohol (e.g., methanol) yields the corresponding benzazepine having the formula

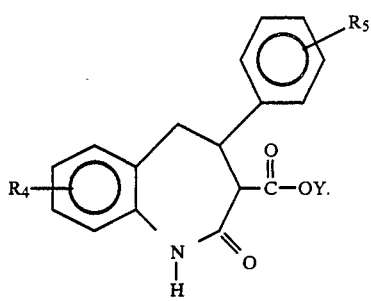

Reaction of a compound of formula VI with a strong base (e.g., lithium diisopropylamide or potassium hexamethyldisilazide) in an etheral solvent, such as tetrahydrofuran, at a reduced temperature followed by the addition of an alkylating agent (e.g., a compound

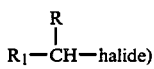

yields a compound having the formula

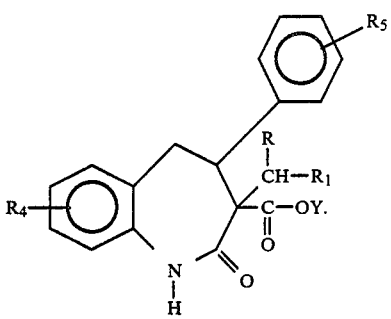

In some instances, the alkylation reaction may proceed more completely if the nitrogen atom in the benzazepine nucleus of a compound of formula VI is first protected from participation in the reaction; e.g., by treatment of a benzazepine of formula VI with a base such as sodium hydride followed by reaction with an alkoxymethyl bromide. After the alkylation reaction has been completed, the nitrogen protecting group is removed.

The preparation of a compound of formula VII from a compound of formula IV can be accomplished by alternate methodology. Alkylation of a compound of formula IV by treatment with a base such as sodium hydride followed by reaction with an alkylating agent (e.g., a compound

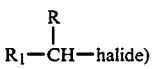

yields a compound having the formula

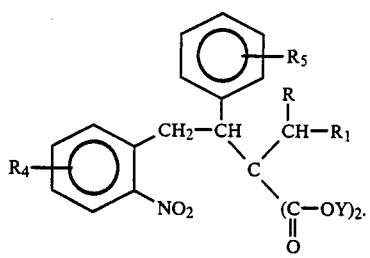

VIII

Reduction of a compound of formula VIII yields the corresponding compound having the formula

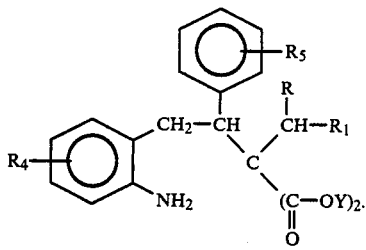

IX

The reduction can be accomplished using a chemical reducing agent (e.g., ferrous sulfate or stannous chloride) or by catalytic hydrogenation (using, for example, palladium on charcoal as a catalyst).

Treatment of an amine of formula IX with an alkali metal alkoxide (e.g., sodium methoxide) and an alcohol (e.g., methanol) yields the corresponding benzazepine of formula VII. Benzazepines of formula VII can also be prepared by treatment of a compound of formula IX with a strong base (e.g., potassium hexamethyldisilazide) in a variety of solvents such as dimethylformamide, tetrahydrofuran and toluene.

Decarboxylation of a compound of formula VII can be accomplished by treating the compound with excess lithium iodide in hot pyridine to obtain a mixture of isomers having the formulas

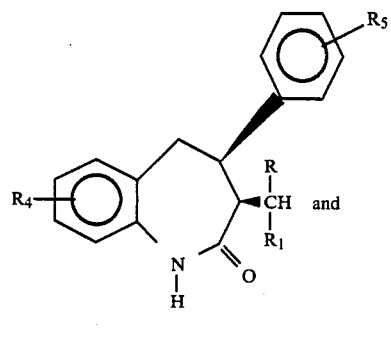

X cis isomer

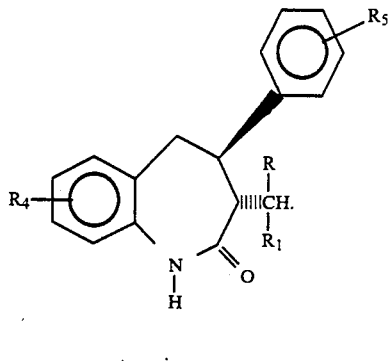

XI trans isomer

The preferred cis isomer is generally the predominant isomer formed during the above reaction. The use of a few drops of water in the above-described reaction mixture increases the ratio of cis isomer to trans isomer. In some cases improved ratios of cis to trans products of formula X and XI by are obtained by treatment of compounds of formula VII with lithium bromide in hot dimethylformamide in the presence of p-aminothiophenol. The isomers can be separated using art recognized techniques such as crystallization or chromatography. Alternatively, the reactions described hereinafter can be run using the diastereomeric mixture (mixture of compounds of formulas X and XI). The isomeric mixture can be separated into its component isomers at any point during the reaction sequence.

Treatment of a compound of formula X or XI with an alkali metal hydride (e.g., sodium hydride) in an inert solvent such as dimethylformamide or dimethylsulfoxide, followed by reaction with a compound having the formula $$halogen-(CH_2)_n-NR_2R_3, \quad XII$$

yields the corresponding compound having the formula

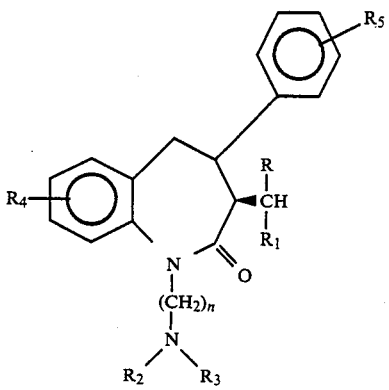

XIII or corresponding trans isomer.

Alternatively, a compound of formula XIII can be prepared by reacting a compound of formula X or formula XI with a compound of formula XII under phase transfer conditions in a mixture of water amd dichloromethane or toluene in the presence of an appopriate base (e.g., barium hydroxide or sodium hydroxide) and catalyst (e.g., benzyl trimethylammonium chloride or tetra-n-butylammonium hydrogen sulfate).

The resolved enantiomers of the compounds of this invention can be prepared by first hydrolyzing a compound of formula VI to obtain the corresponding carboxylic acid having the formula

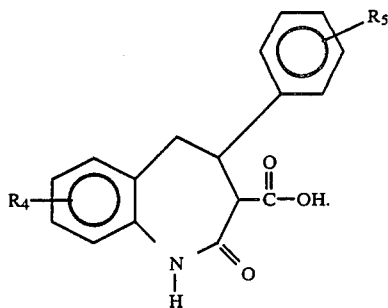

XIV

The hydrolysis can be accomplished, for example, by treating a compound of formula VI with an alkali metal hydroxide in an alcohol (e.g., potassium hydroxide in methanol).

A carboxylic acid of formula XIV can be resolved using a chiral amine. Reaction of the acid and amine in an appropriate solvent yields the diastereomeric salts which can be separated using conventional techniques such as crystallization. Regeneration of the carboxylic acid from the pure diastereomeric salt followed by esterification yields the desired nonracemic form of a compound of formula VI. Alternatively, nonracemic compounds of formula VI can be generated directly from the diastereomeric salts by treatment with an alkyl halide in dimethylformamide in the presence of an inorganic base (e.g., potassium bicarbonate). This nonracemic compound can be converted to the corresponding nonracemic product of formula I via the nonracemic form of intermediates of formulas VII and X or XI using the procedures described above.

Alternatively, compounds of this invention can be prepared as resolved enantiomers by the hydrolysis of a racemic compound of formula X or XI under acidic conditions (e.g., hydrogen chloride in a mixture of water, methanol and tetrahydrofuran) to yield a compound having the formula

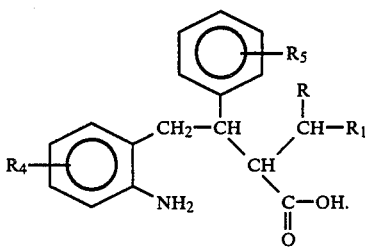

XV

Treatment of a compound of formula XV with an optically pure chiral amine (e.g., (S)-α-methylbenzyl amine) in a suitable solvent (e.g., methanol, ethyl acetate) results in the formation of diasteremeric salts which can be separated using conventional techniques such as crystallization. Regeneration of the carboxylic acid followed by cyclization (e.g., in the presence of dicyclohexylcarbodiimide) affords a single enantiomer of a compound of formula X and XI.

Additional methods for preparing the compounds described herein will be apparent to those skilled in the art. For example, those compounds of formula I wherein $R_1$ is alkyl can be prepared by reducing the corresponding compound of formula X or XI wherein $R_1$ is alkenyl or alkynyl, and then treating the resulting compound with an alkali metal hydride followed by reaction with a compound of formula XII.

In the reactions described above for preparing the compounds of this invention, it may be necessary to protect reactive substituents (e.g., hydroxy and amino) from involvement in the reactions. Protection of the substituents, and the necessary deprotection, can be accomplished using standard techniques. This is further illustrated in the examples showing the preparation of products of formula I wherein $R_2$ and/or $R_3$ are hydrogen.

Preferred members of each of the substituent groups of the benzazepines of formula I are as follows: R and $R_1$ are hydrogen or R is hydrogen and $R_1$ is vinyl or methyl; n is 2; $R_2$ and $R_3$ are each methyl or $R_2$ is hydrogen and $R_3$ is methyl; $R_4$ is halogen or trifluoromethyl (especially 6 or 7-trifluoromethyl) and $R_5$ is p-methoxy.

The following examples are specific embodiments of this invention.

EXAMPLE 1

(cis)-7-Chloro-1-[2-(dimethylamino)ethyl]-1,3,4,5-tetrahydro-4-(4-methoxyphenyl)-3-methyl-2H-1-benzazepin-2-one, monohydrochloride (A)

[2-(5-Chloro-2-nitrophenyl)-1-(4-methoxyphenyl)ethyl]propanedioic acid, dimethyl ester To a stirred mixture of dimethyl p-methoxybenzilidene malonate (40 g, 0.16 mole) and 60% dispersion of sodium hydride (9.6 g, 0.24 mole) in 350 ml of dry dimethylformamide, was added dropwise over 2 hours a solution of 5-chloro-2-nitrotoluene (30 g, 0.176 mole) in 30 ml of dimethylformamide. The reaction was stirred at room temperature for 6 hours, then quenched with glacial acetic acid (15.4 ml, 0.26 mole). The solvent was removed in vacuo and the residue was triturated with water. The yellow solids were filtered and triturated with methanol to yield 50.3 g of a white solid, melting point 128.5°–130.5° C.

(B)

[2-(2-Amino-5-chlorophenyl)-1-(4-methoxyphenyl)ethyl]propanedioic acid, dimethyl ester To a refluxing mixture of [2-(5-chloro-2-nitrophenyl)-1-(4-methoxyphenyl)ethyl]propanedioic acid, dimethyl ester (40 g, 95.0 mmole) and hydrated ferrous sulfate (184.5 g, 0.663 mole) in a (1:10 solution of methanol:water (1.2 L) was added concentrated ammonium hydroxide (142.5 ml) over a 30 minute period. The reaction was stirred at reflux for 20 minutes then cooled to room temperature. Ethyl acetate and Celite were added and the mixture was filtered through Celite. The filtrate was partitioned between ethyl acetate and water. The organic phase was dried over magnesium sulfate and concentrated in vacuo. The product was recrystallized from isopropyl alcohol to yield 28.22 g of the title compound, melting point 114°–116° C.

(C)
7-Chloro-1,3,4,5-tetrahydro-3-(methoxycarbonyl)-4-(4 methoxyphenyl)-2H-1-benzazepin-2-one To a solution of [2-(2-amino-5-chlorophenyl)-1-(4-methoxyphenyl)ethyl]propanedioic acid, dimethyl ester (23.2 g, 59.2 mmole) in methanol (200 ml) was added a 25% solution of sodium methoxide in methanol (16 ml, 69.97 mmole). The solution was refluxed for 3 hours under argon. The reaction was cooled to room temperature and treated with 200 ml 1N hydrochloric acid. A white precipitate was filtered and washed with water, methanol, and dried in vacuo to yield 19.5 g of the title compound, melting point 189°-190.5° C.

(D)
7-Chloro-1,3,4,5-tetrahydro-3-(methoxycarbonyl)-4-(4-methoxyphenyl)-3-methyl-2H-1-benzazepin-2-one To 25 mmole (3 equiv.) of a freshly prepared solution of lithium diisopropylamide in tetrahydrofuran (prepared by addition of 9.6 ml of a 2.6 M solution of n-butyllithium in hexane to 7.5 ml of freshly distilled diisopropylamine in 50 ml of tetrahydrofuran at −78° C.) was added 3.0 g of 7-chloro-1,3,4,5-tetrahydro-3-(methoxycarbonyl)-4-(4-methoxyphenyl)-2H-1-benzazepin-2-one (8.35 mmole). After stirring at −78° C. for 1.5 hours, 1.5 ml of hexamethylphosphoric triamide was added along with 5.9 g of iodomethane (41.7 mmole, 5 equiv.). The reaction mixture was stirred at −78° C. to 20° C. for 6 hours, then quenched with 50 ml of 1N hydrochloric acid. The stirring was continued at 50° C. for 30 minutes. The layers were separated. The aqueous layer was extracted with two 50 ml portions of ethyl acetate. The combined organic layer was washed with two 20 ml portions of saturated sodium bicarbonate, 20 ml of water then dried (magnesium sulfate) and concentrated. The residue was purified on a silica gel column. Elution with 25% ethyl acetate/hexanes gave 1.4 g of 7-chloro-1,3,4,5-tetrahydro-3-(methoxycarbonyl)-4-(4-methoxyphenyl)-3-methyl-2H-1-benzazepin-2-one as a white solid.

(E)
(cis)-7-Chloro-1,3,4,5-tetrahydro-4-(4-methoxyphenyl)-3-methyl-2H-1-benzazepin-2-one A mixture of 800 mg of 7-chloro-1,3,4,5-tetrahydro-3-(methoxycarbonyl)-4-(4-methoxyphenyl)-3-methyl-2H-1-benzazepin-2-one (2.16 mmole), 1.14 g of lithium iodide (8.56 mmoles, 4 equiv.) in 20 ml of pyridine was refluxed for 20 hours. The cooled mixture was diluted with 200 ml of ethyl acetate, then washed with four 30 ml portions of 1N hydrochloric acid, two 30 ml portions of saturated cupric sulfate, 30 ml of water. The organic layer was dried (magnesium sulfate) and concentrated. The residue was triturated with ether to yield 400 mg of (cis)-7-chloro-1,3,4,5-tetrahydro-4-(4-methoxyphenyl)-3-methyl-2H-1-benzazepin-2-one as a white solid.

(F)
(cis)-7-Chloro-1-[2-(dimethylamino)ethyl]-1,3,4,5-tetrahydro-4-(4-methoxyphenyl)-3-methyl-2H-1-benzazepin-2-one, monohydrochloride To a slurry of hexane washed sodium hydride (132 mg of 50% sodium hydride in mineral oil, 2.74 mmole) in 20 ml of dimethylformamide at 25° C. was added 720 mg of (cis)-7-chloro-1,3,4,5-tetrahydro-4-(4-methoxyphenyl)-3-methyl-2H-1-benzazepin-2-one (2.28 mmole). After stirring at 25° C. for 1 hour, the solution turned clear, 6.7 ml of a 1.7 M solution of 2-dimethylaminoethyl chloride (11.4 mmole, 5 equiv.) in toluene was added. The reaction mixture was stirred for 3 hours at 80° C., then cooled to 25° C. and quenched with 1N hydrochloric acid, basified with 1N sodium hydroxide, and extracted with ethyl acetate. The organic layer was dried (magnesium sulfate) and concentrated. The residue was diluted with ether and treated with a saturated solution of hydrochloric acid in ether and concentrated. The residue was triturated with ether and filtered. The solid was washed with ether and dried to give 780 mg of the title compound as a white solid, melting point 228°-231° C.

TLC: silica gel; 10% methanol/dichloromethane; $R_f=0.48$

Analysis Calc'd. for $C_{22}H_{28}N_2O_2Cl \cdot 0.8H_2O$: C, 60.36; H, 6.82; N, 6.40; Cl, 16.20. Found: C, 60.39; H, 6.45; N, 6.32; Cl, 16.40.

EXAMPLE 2

(cis)-7-Chloro-1-[2-(dimethylamino)ethyl]-3-ethyl-1,3,4,5-tetrahydro-4-(4-methoxyphenyl)-2H-1-benzazepin-2-one, monohydrochloride

(A)
7-Chloro-3-ethyl-1,3,4,5-tetrahydro-3-(methoxycarbonyl)-4-(4-methoxyphenyl)-2H-1-benzazepin-2-one To a freshly prepared solution of lithium diisopropylamide in tetrahydrofuran (6 equivalents; prepared by addition of 19.2 ml of a 2.6M solution of n-butyllithium in hexane to 15 ml of freshly distilled diisopropylamine in 80 ml of tetrahydrofuran) at −78° C., was added 3.0 g (8.35 mmole) of 7-chloro-1,3,4,5-tetrahydro-3-(methoxycarbonyl)-4-(4-methoxyphenyl)-2H-1-benzazepin-2-one (see Example 1C. After stirring at −78° C. for 1.5 hours, 3 ml of hexamethylphosphoric triamide was added along with 13.6 ml of iodoethane (filtered through alumina to remove iodine). The mixture was stirred at −78° C. for 30 minutes (under argon), and then at −20° C. (dry-ice/carbon tetrachloride bath) for six days. The reaction was quenched with 1N hydrochloric acid (50 ml), and the aqueous layer was extracted with ethyl acetate (three times). The ethyl acetate extracts and the tetrahydrofuran were combined, washed with saturated sodium bicarbonate and saturated sodium chloride, and dried (magnesium sulfate). The solution was concentrated, combined with 0.31 g of previously prepared crude product and flash chromatographed (silica gel/3:1-hexane:ethyl acetate) yielding 0.61 g of product.

(B)
7-Chloro-3-ethyl-1,3,4,5-tetrahydro-4-(4-methoxyphenyl)-2H-1-benzazepin-2-one Lithium iodide (0.65 g; 4.84 mmole) was added to 7-chloro-3-ethyl-1,3,4,5-tetrahydro-3-(methoxycarbonyl)-4-(4-methoxyphenyl)-2H-1-benzaepin-2-one (0.47 g; 1.21 mmole) in pyridine (15 ml) and water (three drops) and refluxed with stirring for 33 hours. The mixture was cooled, dissolved into ethyl acetate and washed with 1N hydrochloric acid (three times). The combined ethyl acetate layers were dried (magnesium sulfate) and concentrated giving 0.40 g of crude material. This material was combined with another batch of crude (0.49 g, total); flash chromatography purification (silica gel/1:1-hexane:ethyl acetate) gave 0.38 g of the title compound.

(C)
(cis)-7-Chloro-1-[2-(dimethylamino)ethyl]-3-ethyl-1,3,4,5-tetrahydro-4-(4-methoxyphenyl)-benzazepin-2-one, monohydrochloride To a slurry of prewashed (hexane) sodium hydride (~50% in mineral oil) (0.064 g; 1.34 mmole; 1.2 eq.) in dry dimethylformamide (10 ml) was added 7-chloro-3-ethyl-1,3,4,5-tetrahydro-4-(4-methoxyphenyl)-2H-1-benzazepin-2-one (370 mg; 1.12 mmole). After stirring the mixture at 25° C. for 1 hour, 3.2 ml (5.6 mmole) of 1.7N N,N-dimethyl-2-chloroethylamine (in toluene) was added, and the solution was heated at 80° C. for 24 hours. The reaction was quenched with 1N hydrochloric acid, made basic with 50% sodium hydroxide solution, extracted with ethyl acetate (two times) and dried (magnesium sulfate). After solvent removal, 0.49 g of a brown oil remained. This crude product was flash chromatographed (silica gel/3:1-hexane:ethyl acetate, followed by 2:1-hexane: ethyl acetate, followed by 1:1-hexane: ethyl acetate, followed by ethyl acetate). Those fractions which contained the cis amine product were dissolved into ether. The salt was precipitated out by the dropwise addition of hydrogen chloride saturated ether solution. The resultant white solid was collected by suction-filtration, yielding 200 mg. The lower $R_f$ trans isomer of the title compound was likewise obtained (10 mg) as well as a cis-trans mixture (50 mg), and unreacted starting material (40 mg).

Analysis Calc'd for $C_{23}H_{29}ClN_2O_2 \cdot HCl \cdot 0.23 H_2O$ C, 62.56; H, 6.95; N, 6.36; Cl, 16.06. Found: C, 62.56; H, 6.80; N, 6.22; Cl, 16.00.

EXAMPLE 3

(cis)-7-Chloro-1-[2-(dimethylamino)ethyl]-1,3,4,5-tetrahydro-4-(4-methoxyphenyl)-3-(2-propenyl)-2H-1-benzazepin-2-one, monohydrochloride (A)
7-Chloro-1,3,4,5-tetrahydro-3-(methoxycarbonyl)-1-(methoxymethyl)-4-(4-methoxyphenyl)-2H-1-benzazepin-2-one To a solution of 7-chloro-1,3,4,5-tetrahydro-3-(methoxycarbonyl)-4-(4-methoxyphenyl)-2H-1-benzazepin-2-one (270 mg; 0.75 mmole; see Example 1C) in dimethylformamide (10 ml), cooled at 0°–5° C. in an ice-water bath, was added 50% sodium hydride (72 mg; 1.5 mmole). After stirring at 0°–5° C. for 15 minutes, methoxymethylbromide (240 μ; 3 mmole) was added dropwise. The reaction mixture was allowed to stir at 0°–5° C. for two additional hours. The excess sodium hydride was destroyed by the addition of water, and the resulting mixture was extracted with ether. The aqueous layer was extracted with ether (three times) and the combined organic layers were dried (magnesium sulfate) and concentrated. The crude residue was flash chromatographed (silica gel/5–20% ethyl acetate:hexane) yielding 233 mg of the title compound as an oil.

(B)
7-Chloro-1,3,4,5-tetrahydro-3-(methoxycarbonyl)-1-(methoxymethyl)-4-(4-methoxyphenyl)-3-(2-propenyl)-2H-1-benzazepin-2-one To a suspension of 50% sodium hydride (48 mg; 1 mmole) in dimethylformamide (5 ml) cooled at 0°–5° C. was added dropwise a solution of 7-chloro-1,3,4,5-tetrahydro-3-(methoxycarbonyl)-1-(methoxymethyl)-4-(4-methoxyphenyl)-2H-1-benzazepin-2-one (102 mg; 0.25 mmole) in dimethylformamide (1 ml). After stirring at 0°–5° C. for 20 minutes, allyl bromide (360 μl; 4 mmole) was added dropwise, and the reaction mixture was allowed to stir at 0° C. to room temperature for two hours. Excess sodium hydride was destroyed with water, and the mixture was extracted with ether. The aqueous layer was extracted with ether (two times), and the combined organic layers were dried (magnesium sulfate) and concentrated. The crude residue was triturated with hexane (20 ml) to obtain 93 mg of white, crystalline title compound. [The mother liquor contained additional product].

(C)
7-Chloro-1,3,4,5-tetrahydro-3-(methoxycarbonyl)-4-(4-methoxyphenyl)-3-(2-propenyl)-21H-11-benezaepin-2-one To a suspension of 7-chloro-1,3,4,5-tetrahydro-3-(methoxycarbonyl)-1-(methoxymethyl)-4-(4-methoxyphenyl)-3-(2-propenyl)-2H- 1-benzazepin-2-one (715 mg, 1.61 mmole) in methanol (40 ml) was added concentrated sulfuric acid (6 ml) with stirring. The reaction mixture was refluxed (bath temperature 75°–80° C.) for 8 hours, and was then diluted with dichloromethane. The sulfuric acid was carefully neutralized by the addition of saturated sodium bicarbonate solution. The mixture was extracted with dichloromethane (two times) and the combined extracts were dried over anhydrous magnesium sulfate. The concentrated solution was flash chromatographed (silica gel/10–30% ethyl acetate: hexane) to obtain 700 mg of the title compound.

(D)
7-Chloro-1,3,4,5-tetrahydro-4-(4-methoxyphenyl)-3-(2-propenyl)-2H-1-benzazepin-2-one Lithium iodide (0.90 g; 6.7 mmole) was added to 7-chloro-1,3,4,5-tetrahydro-3-(methoxycarbonyl)-4-(4-methoxyphenyl)-3-(2-propenyl)-2H-1-benzazepin-2-one (670 mg; 1.68 mmole) in pyridine (5 ml), three drops of water were added, and the mixture was refluxed with stirring overnight. The solution was dissolved into ethyl acetate and washed with 1N hydrochloric acid (three times). The organic layer was dried (magnesium sulfate) and concentrated. The crude, brownish solid was dissolved into ethyl acetate and suction-filtered through a pad of silica gel (to remove some of the brown color). The silica gel was rinsed several times with ethyl acetate, and the organic solution was concentrated and vacuum dried, leaving 0.52 g of the title compound as an off-white solid.

(E)
(cis)-7-Chloro-1-[2-(dimethylamino)ethyl]-1,3,4,5-tetrahydro-4-(4-methoxyphenyl)-3-(2-propenyl)-2H-1-benzazepin-2-one, monohydrochloride To a slurry of washed (hexane) sodium hydride (~50% in mineral oil) (0.09 g; 1.83 mmole; 1.2 eq.) in dimethylformamide (13 ml) was added 7-chloro-1,3,4,5-tetrahydro-4-(4-methoxyphenyl)-3-(2-propenyl)-2H-1-benzazepin-2-one (520 mg; 1.52 mmole) with stirring. After one hour stirring at 25° C., 1.7N N,N-dimethyl-2-chloroethylamine (in toluene) (4.5 ml; 7.60 mmole) was added, and the mixture was heated to 80° C. with stirring for three hours. The reaction was quenched with 1N hydrochloric acid. The mixture was then made basic with 50% sodium hydroxide solution, extracted with ethyl acetate (two times), dried (magnesium sulfate), concentrated and dried in vacuo. The crude material was flash chromatographed (silica gel/1% methanol:dichloromethane, followed by 2% methanol:dichloromethane). The cis isomer containing fractions were combined and concentrated giving ~400 mg of semi-solid. The residue was coevaporated with ether producing 310 mg of a fluffy white solid. This material was dissolved in ether and hydrogen chloride saturated ether was added, giving a white precipitate that was collected by suction-filtration yielding 200 mg of the title compound. A cis/trans mixture and some pure trans product were also obtained from the flash chromatography.

Analysis Calc'd for $C_{24}H_{29}ClN_2O_2 \cdot HCl$:
C, 64.14; H, 6.73; N, 6.23; Cl, 15.78.
Found: C, 63.92; H, 6.72; N, 6.13; Cl, 15.74.

EXAMPLE 4

(cis,)-1-[2-(Dimethylamino)ethyl]-1,3,4,5-tetrahydro-4-(4-methoxyphenyl)-3-methyl-7-(trifluoromethyl)-2H-1-benzazepin-2-one, monohydrochloride (A)

[2-(2-Nitro-5-trifluoromethylphenyl)-1-(4-methoxyphenyl)ethyl]propanedioic acid, dimethyl ester To a two liter three-neck flask (under nitrogen) was added 67.0 g (0.293 mol) of dimethyl p-methoxybenzylidene malonate and 450 ml of dimethylformamide. The stirred solution was treated with 18.7 g (0.39 mole) of a 50% sodium hydride dispersion. This mixture was treated dropwise with a solution of 60.5 g (0.253 mol) of 2-nitro-5-(trifluoromethyl)toluene in 50 ml of dimethylformamide, over a period of one hour while maintaining the temperature at 28°–32° C. (near the end of the addition, the temperature rose to 38° C. and was rapidly cooled to 30° C.). This mixture was stirred for four hours at room temperature, cooled, treated portionwise with 25 ml of acetic acid and poured onto 2.5 liters of ice water. The mixture was extracted with 250 ml of dichloromethane (three times), dried (magnesium sulfate), filtered and the solvent evaporated to give 126 g of a pale brown semi-solid. The latter was dissolved in 270 ml of methanol, cooled and filtered to give 72.8 g of a pale yellow product, melting point 110°–112° C., $R_f$=0.74 (1:1 ethyl acetate-hexane). A sample recrystallized from methanol, melted at 111°–113° C.

(B)

α-Methyl-[2-(2-nitro-5-trifluoromethylphenyl)-1-(4-methoxyphenyl)ethyl]propanedioic acid, dimethyl ester

[2-(2-Nitro-5-trifluoromethylphenyl)-1-(4-methoxyphenyl)ethyl]propanedioic acid, dimethyl ester (7.00 g; 15.4 mmole) was dissolved in dry dimethylformamide (35 ml) under argon. Prewashed (hexane) 50% sodium hydride (0.89 g; 18.4 mmole) was added with stirring. Stirring was continued for 20 minutes before iodomethane (filtered through alumina) (11.6 g; 5.1 ml; 81.5 mmole; sp. gr.=2.24–2.27; 5 eq.) was added dropwise. The mixture was allowed to stir a total of 4.5 hours. The solution was partitioned between ethyl acetate and 1N hydrochloric acid, and the organic layer was collected and washed again with 1N hydrochloric acid, saturated potassium carbonate, saturated sodium chloride, and dried (magnesium sulfate). The concentrated residue was flashed (silica gel/9:1-hexane:ethyl acetate, followed by 8:2-hexane:ethyl acetate). The product was collected from the appropriate fractions and concentrated giving 6.90 g of the title compound as a viscous oil.

(C)

α-Methyl-[2-(2-amino-5-trifluoromethylphenyl)-1-(4-methoxyphenyl)ethyl]propanedioic acid, dimethyl ester α-Methyl-[2-(2-nitro-5-trifluoromethylphenyl)-1-(4-methoxyphenyl)ethyl]propanedioic acid, dimethyl ester (6.80 g; 14.9 mmole) was dissolved in methanol (200 ml) under argon at room temperature. Powdered stannous chloride dihydrate (17.48 g; 77.5 mmole) was added, followed by concentrated hydrochloric acid (19 ml) with stirring. After 1.5 hours, Celite, ethyl acetate and saturated potassium carbonate solution were added with stirring (the potassium carbonate was added portionwise). The suspension was filtered through a Celite pad. The pad was then rinsed with ethyl acetate (three times). The filtrate was concentrated and the resulting white solid was triturated with 10% methanol:water and dried giving 6.02 g of the title compound.

(D)

1,3,4,5-Tetrahydro-3-(methoxycarbonyl)-4-(4-methoxyphenyl)-3-methyl-7-(trifluoromethyl)-2H-1-benzazepin-2-one A 25% (by weight) sodium methoxide in methanol solution (14.2 ml; 625 mmole; 4.6 eq.; d=0.945) and α-methyl-[2-(2-amino-5-trifluoromethylphenyl)-1-(4-methoxyphenyl)ethyl]propanedioic acid, dimethyl ester (5.96 g; 13.56 mmole) in methanol (30 ml) and dry dimethylformamide (35 ml) were refluxed (~95° C.) overnight. 1N Hydrochloric acid was added with stirring producing a white precipitate that was collected by suction-filtration, washed with water (three times) and dried in vacuo giving 4.88 g of a white solid which contained an impurity as shown by NMR. The impurity disappeared after the sample stood overnight.

(E)

1,3,4,5-Tetrahydro-4-(methoxyphenyl)-3-methyl-7-(trifluoromethyl)-2H-1-benzazepin-2-one Lithium iodide (5.26 g; 39.3 mmole) was added to 1,3,4,5-tetrahydro-3-(methoxycarbonyl)-4-(methoxyphenyl)-3-methyl-7-(trifluoromethyl)-2H-1-benzazepin-2-one (4.00 g; 9.82 mmole) in pyridine (40 ml) (five drops of water were added) and the mixture was refluxed with stirring for 8.5 hours. The solution was dissolved in ethyl acetate and washed with 1N hydrochloric acid (three times). The organic layer was dried (magnesium sulfate) and concentrated giving 3.43 g of the title compound as a solid.

(F)

(cis)-1-[2-(Dimethylamino)ethyl]-1,3,4,5-tetrahydro-4-(4-methoxyphenyl)-3-methyl-7-(trifluoromethyl)-2H-1-benzazepin-2-one, monohydrochloride To a solution of 1,3,4,5-tetrahydro-4-(methoxyphenyl)-3-methyl-7-(trifluoromethyl)-2H-1-benzazepin-2-one (3.37 g; 9.65 mmole) in dry dimethylformamide 75 ml) was added prewashed (hexane) 50% sodium hydride (5.56 g; 11.58 mmole; 1.2 eq.) with stirring. After ~20 minutes, 1.7N (in toluene) N,N-dimethyl-2-chloroethylamine (24.0 ml; 40.8 mmole) was added, and the mixture was heated at 85° C. for four hours. The mixture was made basic with 50% sodium hydride, and extracted with ethyl acetate (three times). The combined organics were dried (magnesium sulfate) and concentrated, and the dark oily residue was placed under vacuum. The crude material was flash chromatographed (silica gel/1% methanol:dichloromethane, followed by 3% methanol:dichloromethane). The acidified (hydrogen chloride saturated ether) product weighed 1.06 g.

Analysis Calc'd for $C_{23}H_{27}F_3N_2O_2 \cdot H_2O \cdot HCL$: C, 58.10; H, 6.36; N, 5.89; Cl, 7.46; F, 12.0. Found: C, 58.10; H, 5.90; N, 5.75; Cl, 7.94; F, 11.5.

EXAMPLE 5

(cis)-1-[2-(Dimethylamino)ethyl]-1,3,4,5-tetrahydro-4-(4-methoxyphenyl)-3-(2-propenyl)-7-trifluoromethyl)-2H-1-benzazepin-2-one, monohydrochloride

Method I (A)

[2-(2-Amino-5-trifluoromethylphenyl)-1-(4-methoxyphenyl)ethyl]propanedioic acid, dimethyl ester A suspension of 25.0 g (0.055 mol) of [2-(2-nitro-5-trifluoromethylphenyl)-1-(4-methoxyphenyl)ethyl]-propanedioic acid, dimethyl ester (see Example 4A) in 200 ml of methanol was treated with a cold suspension of 2.5 g of 5% palladium on charcoal in 50 ml of methanol (under nitrogen) and placed on the Parr apparatus at 58 lbs. of hydrogen. The theoretical amount of hydrogen was consumed in about 30 minutes and this mixture was then heated at 50°–55° C. for one hour to assure that all of the nitro compound had dissolved. The mixture was removed from the Parr and allowed to stand at room temperature overni-ght. The flask was heated to dissolve the crystallized product, and the hot solution was filtered through Celite (under nitrogen) and washed with hot methanol. The colorless filtrate was concentrated on a rotary evaporator to give 22.2 g of a nearly colorless solid. The latter was triturated with 100 ml of hexane and then with 50 ml of hexane. The solvent was decanted and the entrained solvent removed on a rotary evaporator to give 21.3 g of product, melting point 124°–127° C. A sample of this material, after crystallization from methanol, melted at 125°–127° C.

(B)

1,3,4,5-Tetrahydro-3-(methoxycarbonyl)-4-(methoxyphenyl)-7-(trifluoromethyl)-2H-1-benzazepin-2-one Under an argon atmosphere, a stirred solution of [2-(2-amino-5-trifluoromethylphenyl)-1-(4-methoxyphenyl)ethyl]propanedioic acid, dimethyl ester (20.0 g; 0.047 mol) in 200 ml of methanol was treated with 13.3 ml of 25% sodium methoxide in methanol and heated to reflux. After about 2.75 hours of heating, the mixture was cooled in ice water and 1N hydrochloric acid was added to precipitate the product. Stirring in an ice water bath, followed by filtering, washing with water and air-drying yielded 19.0 g of product. The product was suspended in 30 ml of isopropanol, allowed to stand for one hour, filtered and washed with isopropanol and hexane to yield 13.64 g of the title compound, melting point 161°–163° C.

(C)

1,3,4,5-Tetrahydro-3-(methoxycarbonyl)-1-(methoxymethyl)-4-(methoxyphenyl)-7-(trifluoromethyl)-2H-1-benzazepin-2-one To a suspension of sodium hydride (360 mg; 7.5 mmole; 50% oil dispersion/prewashed with dry ether several times) in dry dimethylformamide (30 ml), cooled at 0°–5° C. was added a solution of 1,3,4,5-tetrahydro-3-(methoxycarbonyl)-4-(methoxyphenyl)-7-(trifluoromethyl)-2H-1-benzazepin-2-one (1.9 g; 5 mmole) in dry dimethylformamide (15 ml) dropwise and with stirring. The mixture was stirred for an additional 20 minutes at 0°–5° C., whereupon bromomethylmethyl ether (800 μl; 10 mmole) was added dropwise, and stirring was continued at this temperature for an additional hour. Excess sodium hydride was destroyed by the addition of water, and the mixture was diluted with ether and washed with water. The aqueous layer was extracted with ether (three times) and the combined extracts were dried (magnesium sulfate) and concentrated. The crude oily residue was flash chromatographed (silica gel/5–25% ethyl acetate:hexane) to obtain 1.67 g of the title compound as an oil.

(D)

1,3,4,5-Tetrahydro-3-(methoxycarbonyl)-1-(methoxymethyl)-4-(methoxyphenyl)-3-(2-propenyl)-7-(trifluoromethyl)-2H-1-benzazepin-2-one To a suspension of sodium hydride (384 mg; 8 mmole; 50% oil dispersion) in dry dimethylformamide (35 ml), cooled in an ice water bath, was added a solution of 1,3,4,5-tetrahydro-3-(methoxycarbonyl)-1-(methoxymethyl)-4-(methoxyphenyl)-7-(trifluoromethyl)-2H-1-benzazepin-2-one (917 mg; 21 mmole) in dimethylformamide (8 ml) with stirring. After stirring at 0°–5° C. for 30 minutes, allyl bromide (1.5 ml) was added in one portion, the mixture was allowed to stand at 0°–5° C. for three additional hours, whereupon excess hydride was destroyed by the addition of water. The mixture was diluted with ether and washed with water. The aqueous layer was extracted with ether (three times), and the combined ether extracts were dried (magnesium sulfate) and concentrated. The crude residue was flash chromatographed (silica gel/5–20% ethyl acetate:hexane) to obtain 905 mg of the title compound in crystalline form.

(E)

1,3,4,5-Tetrahydro-3-(methoxycarbonyl)-4-(methoxyphenyl)-3-(2-propenyl)-7-(trifluoromethyl)-2H-1-benzazepin-2-one Concentrated sulfuric acid (8 ml) and anhydrous lithium bromide (720 mg; 8 mmole) were added to a suspension of 1,3,4,5-tetrahydro-3-(methoxycarbonyl)-1-(methoxymethyl)-4-(methoxyphenyl)-3-(2-propenyl)-7-(trifluoromethyl)-2H-1-benzazepin-2-one (905 mg; 1.9 mmole) in methanol (40 ml) with stirring. The reaction mixture was heated under reflux (bath temperature=8-0°–85° C.) for nine hours, and then allowed to stand overnight at room temperature. The acid was carefully neutralized by the addition of saturated sodium bicarbonate solution and extracted with ethyl acetate (three times). The combined organic layers were dried (magnesium sulfate) and concentrated yielding 858 mg of the title compound as a solid.

(F)

1,3,4,5-Tetrahydro-4-(methoxyphenyl)-3-(2-propenyl)-7-(trifluoromethyl)-2H-1-benzazepin-2-one Lithium iodide (1.08 g; 8.04 mmole) was added to 1,3,4,5-tetrahydro-3-(methoxycarbonyl)-4-(methoxyphenyl)-3-(2-propenyl)-7-(trifluoromethyl)-2H-1-benzazepin-2-one (870 mg; 2.01 mmole) in pyridine (14 ml), three drops of water were added, and the mixture was refluxed with stirring for 6.5 hours. The solution was dissolved into ethyl acetate and washed with 1N hydrochloric acid (three times). The organic layer was dried (magnesium sulfate) and concentrated giving 0.79 g of solid. The crude material was used "as is" in the next step.

(G)
(cis)-1-[2-(Dimethylamino)ethyl]-1,3,4,5-tetrahydro-4-(4-methoxyphenyl)-3-(2-propenyl)-7-trifluoromethyl)-2H-1-benzazepin-2-one, monohydrochloride To a slurry of washed (hexane) sodium hydride (~50% in mineral oil) (0.10 g; 2.11 mmole) in dimethylformamide (13 ml) was added 1,3,4,5-tetrahydro-4-(methoxyphenyl)-3-(2-propenyl)-7-(trifluoromethyl)-2H-1-benzazepin-2-one (660 mg; 1.76 mmole) with stirring. After one hour at 25° C., 1.7N N,N-dimethyl-2-chloroethylamine (in toluene) (5.2 ml; 8.80 mmole) was added, and the mixture was heated to 80° C. with stirring overnight. The mixture was quenched with 1N hydrochloric acid, made basic with 50% sodium hydroxide solution, extracted with ethyl acetate (two times) and dried (magnesium sulfate). The concentrated crude mixture weighed 0.77 g. The solid was flash chromatographed (silica gel/1% methanol:dichloromethane, followed by 2% methanol:dichloromethane, followed by 3% methanol:dichloromethane). Appropriate fractions contained the desired cis free amine product, which was collected (rotary evaporated fractions) and dissolved in ether. Some ether insoluble material (presumably silica gel) was filtered off and the filtrate was treated with hydrogen chloride saturated ether. The resulting precipitate was collected by suction-filtration and rinsed with ether. The title compound weighed 190 mg. A mixture of cis/trans product as well as pure trans product were also obtained from the flash chromatography.

Analysis Calc'd for $C_{25}H_{29}F_3N_2O_2.HCl.0.44H_2O$: C, 61.17; H, 6.34; N, 5.71; Cl, 7.22; F, 11.61. Found: C, 61.17; H, 6.07; N, 5.58; Cl, 6.98; F, 11.32.

Method II

(A)
α-(2-Propenyl)-[2-(2-nitro-5-trifluoromethylphenyl)-1-(4-methoxyphenyl)ethyl]propanedioic acid, dimethyl ester

[2-(2-Nitro-5-trifluoromethylphenyl)-1-(4-methoxyphenyl)ethyl]propanedioic acid, dimethyl ester (46.54 g; 0.102 mole; see Example 4A) was dissolved in dry dimethylformamide (290 ml) under argon. Fifty percent sodium hydride (5.89 g; 0.123 mole; prewashed-hexane) was added with stirring which was continued for 20 minutes before allyl bromide (44 ml; 61.7 g; 0.510 mmole; d=1.398; 5 eq.) was added dropwise. After six hours, 40 minutes, the reaction was quenched with 1N hydrochloric acid. The solution was extracted with ethyl acetate (two times) and the extract was washed with 1N hydrochloric acid (two times), saturated potassium carbonate (two times), saturated sodium chloride, and dried (magnesium sulfate). The concentrated solution (viscous oil) was flash chromatographed (silica gel/9:1-hexane: ethyl acetate, followed by 8:2-hexane:ethyl acetate) in two portions. After drying in vacuo overnight, the yellow viscous oil product weighed 54.77 g. The product was used "as is" in the next step.

(B)
-(2-Propenyl)-[2-(2-amino-5-trifluoromethylphenyl)-1-(4-methoxyphenyl)ethyl]propanedioic acid, dimethyl ester α-(2-Propenyl)-[2-(2-nitro-5-trifluoromethylphenyl)-1-(4-methoxyphenyl)ethyl]propanedioic acid, dimethyl ester (50.49 g; 0.102 mole) was dissolved in methanol (350 ml) under argon at room temperature. Powdered stannous chloride dihydrate (119.67 g; 0.53 mole; 5.2 eq.) was added followed by concentrated hydrochloric acid (155 ml with stirring. Celite, ethyl acetate, and saturated potassium carbonate solution were added with stirring (the potassium carbonate was added portionwise). The suspension was filtered through a Celite pad (rinsed three times with ethyl acetate), rotary evaporated, and suction-filtered. The collected white solid was rinsed with 10% methanol:water and dried giving 51.97 g of the title compound.

(C)
1,3,4,5-Tetrahydro-3-(methoxycarbonyl)-4-(methoxyphenyl)-3-(2-propenyl)-7-(trifluoromethyl)-2H-1-benzazepin-2-one α-(2-Propenyl)-[2-(2-amino-5-trifluoromethylphenyl)-1-(4-methoxyphenyl)ethyl]propanedioic acid, dimethyl ester (47.47 g; 0.102 mole) and a 25% (by weight) solution of sodium methoxide in methanol (107 ml; 0.469 mole; d=0.945; 4.6 eq.) in methanol (200 ml) and dry dimethylformamide (200 ml) was refluxed (~95° C.) overnight. 1N Hydrochloric acid was added with stirring, producing a precipitate that was collected by suction-filtration and triturated with water (two times). The solid was slurried in carbon tetrachloride and rotary evaporated followed by vacuum drying to give 42.99 g of crude product.

(D)
1,3,4,5-Tetrahydro-4-(4-methoxyphenyl)-3-(2-propenyl)-7-(trifluoromethyl)-2H-1-benzazepin-2-one Lithium iodide (13.75 g; 102.6 mmole) was added to 1,3,4,5-tetrahydro-3-(methoxycarbonyl)-4-(methoxyphenyl)-3-(2-propenyl)-7-(trifluoromethyl)-2H-1-benzazepin-2-one (42.94 g; 99 mmole) in pyridine (300 ml), a few drops of water were added, and the mixture was refluxed with stirring for two days. Pyridine was vacuum distilled off and the nearly dry residue was dissolved in chloroform and washed with 1N hydrochloric acid (four times), saturated sodium chloride, and dried (magnesium sulfate). The organic solution was concentrated and vacuum dried overnight, yielding 35.12 g of reddish crude product. This material was triturated with methanol leaving 19.87 g of the title compound as a solid.

(E)
(cis)-1-[2-(Dimethylamino)ethyl]-1,3,4,5-tetrahydro-4-(4-methoxyphenyl)-3-(2-propenyl)-7-trifluoromethyl)-2H-1-benzazepin-2-one, monohydrochloride To a slurry of prewashed sodium hydride (320 mg of 60% sodium hydride in mineral oil) in 30 ml of dimethylformamide at 25° C. was added 2.5 g of 1,3,4,5-tetrahydro-4-(4-methoxyphenyl)-3-(2-propenyl)-7-(trifluoromethyl)-2H-1-benzazepin-2-one. After stirring at 25° C. for one hour, 4.65 ml of a 2.15M solution of 2-dimethylaminoethyl chloride (9.99 mmole, 1.5 equiv.) in toluene was added. The reaction mixture was stirred for three hours at 80° C., then cooled to 25° C. and quenched with 1N hydrochloric acid, basified with 1N sodium hydroxide, and extracted with ethyl acetate. The organic layer was dried (magnesium sulfate) and concentrated, and the residue was flash chromatographed on a prewashed silica gel column. The appropriate fractions were combined, concentrated, and vacuum dried overnight giving 1.92 g of free amine product. This material was dissolved in ether and hydrogen chloride saturated ether was added yielding 2.08 g of the title compound.

Analysis Calc'd for $C_{25}H_{29}F_3N_2O_2 \cdot HCl \cdot 0.22H_2O$: C, 61.66; H, 6.30; N, 5.75; Cl, 7.28; F, 11.70. Found: C, 61.66; H, 6.15; N, 5.73; Cl, 7.17; F, 11.46.

EXAMPLE 6

(cis)-1-[2-(Dimethylamino)ethyl]-1,3,4,5-tetrahydro-4-(4-methoxyphenyl)-3-propyl-7-(trifluoromethyl)-2H-1-benzazepin-2-one, monohydrochloride (A)

1,3,4,5-Tetrahydro-4-(4-methoxyphenyl)-3-propyl-7-(trifluoromethyl)-2H-1-benzazepin-2-one 1,3,4,5-Tetrahydro-4-(4-methoxyphenyl)-3-(2-propenyl)-7-(trifluoromethyl)-2H-1-benzazepin-2-one (3.50 g; 9.32 mmole; see Example 5, Method II, part D) was dissolved in glacial acetic acid (100 ml) and trifluoroacetic acid (50 ml). Palladium on charcoal (0.71 g) was added to the degassed solution, and the mixture was placed on a Parr apparatus for four hours. The solution was then filtered through a pad of Celite and the Celite was rinsed several times with ethyl acetate. The concentrated mixture was vacuum dried yielding 3.53 g of the title compound as a solid.

(B)

(cis)-1-[2-(Dimethylamino)ethyl]-1,3,4,5-tetrahydro-4-(4-methoxyphenyl)-3-propyl-7-(trifluoromethyl)-2H-1-benzazepin-2-one, monohydrochloride Potassium bicarbonate (1.86 g; 18.5 mmole), 1,3,4,5-tetrahydro-4-(4-methoxyphenyl)-3-propyl-7-(trifluoromethyl)-2H-1-benzazepin-2-one (3.50 g 9.27 mmole), and potassium iodide (catalytic amount) were suspended in methylethyl ketone (55 ml). 2-Dimethylaminoethyl chloride (5.5 ml of 2.15M solution in toluene; 11.9 mmole) was added with stirring, and the mixture was refluxed for one hour. An additional 5.5 ml of 2-dimethylaminoethyl chloride was added and reflux was continued for two hours. Dimethylformamide (10 ml) was added and after an additional four hours of reflux, the solution was rotary evaporated and dimethylformamide was removed using a high vacuum pump. The residue was partitioned between ethyl acetate/water, and the organic layer was dried (magnesium sulfate) and concentrated. The crude free amine of the title compound (4.29 g) was flash chromatographed using 0.1–2.0% methanol:dichloromethane, yielding 2.28 g of product. This product was converted to the title hydrochloride salt using hydrogen chloride saturated ether; melting point 233.5°–235° C.

Analysis Calc'd for $C_{25}H_{31}F_3N_2O_2 \cdot HCl$: C, 61.91; H, 6.65; N, 5.78; Cl, 7.31; F, 11.75. Found C, 61.79; H, 6.31; N, 5.73; Cl, 7.05; F, 11.71.

EXAMPLE 7

(cis)-1-[2-(Dimethylamino)ethyl]-1,3,4,5-tetrahydro-4-(4-methoxyphenyl)-3-(2-propenyl)-6-(trifluoromethyl)2H-1-benzazepin-2-one (A)

[2-(2-Nitro-6-trifluoromethylphenyl)-1-(4-methoxyphenyl)ethyl]propanedioic acid, dimethyl ester To a dry two liter three neck flask was added 52.7 g (0.21 mol) of p-methoxybenzylidene malonate and 350 ml of dimethylformamide. This solution was stirred (under nitrogen), treated with 11.0 g (0.27 mol) of 60% sodium hydride dispersion and this slurry was treated dropwise with a solution of 43.0 g (0.21 mol) of 2-nitro-6-(trifluoromethyl)toluene in 50 ml of dimethylformamide over a period of 30 minutes while maintaining the temperature at 28°–30° C. The mixture was stirred at room temperature for six hours, allowed to stand overnight at room temperature, cooled and treated portionwise with 20 ml of acetic acid. The slurry was poured onto two liters of ice water and extracted with 500 ml of dichloromethane. The aqueous layer was extracted with 250 ml of dichloromethane and then with 100 ml of dichloromethane (two times). The organic phases were combined, extracted with 500 ml of water (three times), dried (magnesium sulfate), filtered and the solvent evaporated to give 99.1 g of a granular solid. This was digested with 150 ml of hot methanol. This suspension was allowed to cool to room temperature, cooled overnight, filtered, washed with cold methanol and dried to give 78.3 g of solid, melting point 117°–119° C.

(B)

α-(2-Propenyl)-[2-(2-nitro-6-trifluoromethylphenyl)-1-(4-methoxyphenyl)ethyl]propanedioic acid, dimethyl ester

[2-(2-Nitro-6-trifluoromethylphenyl)-1-(4-methoxyphenyl)ethyl]propanedioic acid, dimethyl ester (14.55 g; 31.96 mmole) was dissolved in dry dimethylformamide (90 ml) under argon. Prewashed 50% sodium hydride (1.85 g; 38.5 mmole) was added with stirring and stirring was continued for 20 minutes before allyl bromide (19.33 g; 159.8 mmole; 13.8 ml; d=1.398; 5 eq.) was added dropwise. The mixture was quenched (1N hydrochloric acid) after a few minutes of reaction time, and extracted with ethyl acetate (two times). The organic extract was washed with saturated potassium carbonate (two times), saturated sodium chloride, and dried (magnesium sulfate). The solution was concentrated on a high vacuum pump leaving 23.0 g. This material was flash chromatographed (silica gel/9:1-hexane:ethyl acetate) and the appropriate fractions were combined and concentrated giving 15.45 g of the title compound as an oil.

(C)

α-(2-Propenyl)-[2-(2-amino-6-trifluoromethylphenyl)-1-(4-methoxyphenyl)ethyl]propanedioic acid, dimethyl ester α-(2-Propenyl)-[2-(2-nitro-6-trifluoromethylphenyl)-1-(4methoxyphenyl)ethyl]propanedioic acid, dimethyl ester (15.42 g; 31.12 mmole) was dissolved in methanol (110 ml) under argon at room temperature. Powdered stannous chloride dihydrate (36.52 g; 161.8 mmol; 5.2 eq.) was added followed by concentrated hydrochloric acid (50 ml) with stirring. After ~1.5 hours, Celite, ethyl acetate, and saturated potassium carbonate solution were added with stirring (the potassium carbonate solution was added portionwise). The suspension was filtered, and the solid rinsed with ethyl acetate (three times). The filtrate was concentrated, and the residue was washed with 10% methanol/water. The washings were concentrated and dried in vacuo giving ~16 g of a yellow oil. The solids (tin salts, Celite, potassium bicarbonate, etc.) that had been filtered from the reaction mixture were triturated in acetone (several times) and suction filtered through a pad of Celite. The acetone filtrate was concentrated, and the remaining residue was partitioned between choroform and water. The chloroform layer was dried (magnesium sulfate) and concentrated, leaving 9.06 g of the title compound as a solid. The remaining product was assumed to be in the aforementioned and ~16 g of yellow oil. The yellow oil was used "as is" in the next step, as was the 9.06 g of solid.

(D)

1,3,4,5-Tetrahydro-3-(methoxycarbonyl)-4-(methoxyphenyl)-3-(2-propenyl)-6-(trifluoromethyl)-2H-1-benzazepin-2-one α-(2-Propenyl)-[2-(2-amino-6-trifluoromethylphenyl)-1-(4-methoxyphenyl)ethyl]propanedioic acid, dimethyl ester (9.03 g; 19.4 mmole) and a 25% (by weight) sodium methoxide in methanol solution (20.5 ml; 89.5 mmole; d=0.945; 4.6 eq.) in methanol (100 ml) and dry dimethylformamide (100 ml) were refluxed (~95° C. for four hours. 1N Hydrochloric acid was added with stirring, producing a precipitate that was collected by suction-filtration, washed with water (three times) and dried in vacuo giving ~10 g of the title compound as a solid. The "crude" material was used "as is".

(E)

1,3,4,5-Tetrahydro-4-(methoxyphenyl)-3-(2-propenyl)-6-(trifluoromethyl)-2H-1-benzazepin-2-one Lithium iodide (11.98 g; 89.44 mmole) was added to 1,3,4,5-tetrahydro-3-(methoxycarbonyl)-4-(methoxyphenyl)-3-(2-propenyl)-6-(trifluoromethyl)-2H-1-benzazepin-2-one (9.69 g; 22.36 mmole) in pyridine (40 ml) and water (a few drops). The mixture was refluxed with stirring for 11 hours. The pyridine was vacuum distilled off and the residue was dissolved into methanol and washed with 1N hydrochloric acid (three times), and saturated sodium chloride, and dried (magnesium sulfate). The concentrated residue was black indicating some decomposition occurred. The 9.67 g of this black residue was flash chromatographed (silica gel/3:1-hexane:ethyl acetate, followed by 1:1-hexane/ethyl acetate). Appropriate fractions were combined and concentrated giving 5.87 g of the title compound as a solid.

(F)

(cis)-1-[2-(Dimethylamino)ethyl]-1,3,4,5-tetrahydro-4-(4-methoxyphenyl)-3-(2-propenyl)-6fluoromethyl)-2H-1-benzazepin-2-one To 1,3,4,5-tetrahydro-4-(methoxyphenyl)-3-(2-propenyl)-6-(trifluoromethyl)-2H-1-benzazepin-2-one (3.40 g; 9.05 mmole), potassium bicarbonate (1.81 g; 18.1 mmole), and potassium iodide (catalytic amount) suspended in methylethyl ketone (55 ml) was added a 2.15M solution of 2-dimethylaminoethyl chloride (5.1 ml; 10.9 mmole) in toluene, with stirring. After refluxing for ~30 minutes, an additional 5.1 ml of the amine was added, and an additional 1.81 g of potassium bicarbonate was added after 1.5 hours of reflux. After six hours of reflux, the mixture was rotary evaporated and the residue was dissolved into ethyl acetate, and washed with water. The organic layer was dried (magnesium sulfate) and concentrated leaving 4.07 g of viscous, oily free amine of the title compound. This material was flash chromatographed (silica gel/0.5-3% gradient methanol:dichloromethane) and the cis containing fractions were combined and concentrated, dissolved in ether, washed with 1N sodium bicarbonate, dried (magnesium sulfate), and acidified with hydrogen chloride saturated ether. The mixture was concentrated and the white solid triturated in ether. The solid product was collected by suction-filtration, yielding 1.39 g of the title compound; melting point 226°-228° C.

Analysis Calc'd. for $C_{25}H_{30}N_2ClF_3O_2.0.23H_2O$: C, 61.63; H 6.30; N 5.75; F 11.70; Cl 7.28. Found: C, 61.63; H, 6.26; N, 5.62; F, 11.60; Cl, 7.53.

EXAMPLE 8

(cis)-1-[2-(Dimethylamino)ethyl]-1,3,4,5-tetrahydro-4-(4-methoxyphenyl)-3-propyl-6-(trifluoromethyl)-2H-1-benzazepin-2-one, monohydrochloride (A)

1,3,4,5-Tetrahydro-4-(4-methoxyphenyl)-3-propyl-6-(trifluoromethyl)-2H-1-benzazepin-2-one (cis)-1-[2-(Dimethylamino)ethyl]-1,3,4,5-tetrahydro-4-(4-methoxyphenyl)-3-(2-propenyl)-6-(trifluoromethyl)-2H-1-benzazepin-2-one (4.25 g; 11.3 mmole) was dissolved in ethyl acetate (65 ml). Palladium on charcoal (0.86 g) was added to the degassed solution, and the mixture was placed on a Parr apparatus for four hours. The material was filtered through a pad of Celite and concentrated giving 4.3 g of crystalline solid.

(B)

(cis)-1-[2-(Dimethylamino)ethyl]-1,3,4,5-tetrahydro-4-(4-methoxyphenyl)-3-propyl-6-(trifluoromethyl)-2H-1-benzazepin-2-one, monohydrochloride To 1,3,4,5-tetrahydro-4-(4-methoxyphenyl)-3-propyl-6-(trifluoromethyl)-2H-1-benzazepin-2-one (4.23 g; 11.21 mmole), potassium bicarbonate (4.49 g; 44.8 mmole; 4 eq.), and potassium iodide (catalytic amount) suspended in methylethyl ketone (70 ml) was added a 2.15M solution of 2-dimethylaminoethyl chloride (12.6 ml; 27.0 mmole; 2.4 eq.) in toluene with stirring. The mixture was refluxed for 10.5 hours, then concentrated. The residue as dissolved into ethyl acetate and washed with water. The organic layer was dried (magnesium sulfate) and concentrated. The residue was flash chromatographed (silica gel column/0.5% methanol:dichloromethane followed by 2.0% methanol:dichloromethane) and appropriate fractions were combined and concentrated. The residue was dissolved in ether and hydrogen chloride saturated ether was added. The mixture was concentrated, and coevaporated with ether several times. The solid was partitioned between ether and 1N sodium bicarbonate. The ether layer was dried (magnesium sulfate) and concentrated. After standing overnight, the solid residue was much less soluble in ether. The solid was triturated in ether and the mixture was centrifuged and a solid was obtained. Conversion to the hydrochloride salt using hydrogen chloride saturated ether yielded the title compound, melting point 180.5°–182.5° C.

Analysis Calc'd. for $C_{25}H_{31}F_3N_2O_2 \cdot HCl \cdot 0.4H_2O$: C, 60.94; H, 6.71; N, 5.69; Cl, 7.20; F, 11.57. Found: C, 60.94; H, 6.58; N, 5.65; Cl, 7.38; F, 11.32.

EXAMPLE 9

(d-cis)-1-[2-(Dimethylamino)ethyl]-1,3,4,5-tetrahydro-4-(4-methoxyphenyl)-3-(2-propenyl)-6-trifluoromethyl)-2H-1-benzazepin-2-one, monohydrochloride

(A)

[2-(2-Amino-6-trifluoromethylphenyl)-1-(4-methoxyphenyl)ethyl]propanedioic acid, dimethyl ester A suspension of 40.4 g (0.088 mol) of [2-(2-nitro-6-trifluoromethylphenyl)-1-(4-methoxyphenyl)-ethyl] propanedioic acid, dimethyl ester (see Example 7A) in methanol was treated with a cold suspension of 5% palladium on charcoal in methanol (under nitrogen) and placed on the Parr apparatus at 58 psi of hydrogen. The mixture was heated at 50°–55° C. for 1 hour to assure that all of the starting material had dissolved. The mixture was removed from the Parr apparatus and allowed to stand at room temperature overnight. The flask was heated to dissolve the crystallized product, and the hot solution was filtered through Celite (under nitrogen) and washed with hot methanol. The colorless filtrate was concentrated on a rotary evaporator to yield 36.9 g of the title compound, melting point 111°–113° C. A sample crystallized from methanol melted at 112°–114° C.

(B)

1,3,4,5-Tetrahydro-3-(methoxycarbonyl)-4-(methoxyphenyl)-6-(trifluoromethyl)-2H-1-benzazepin-2-one To a dry two liter three-neck flask was added 34.5 g (0.081 mol) of [2-(2-amino-6-trifluoromethylphenyl)-1-(4-methoxyphenyl)ethyl]propanedioic acid, dimethyl ester and 350 ml of methanol. The suspension was heated to 45° C. and the resulting solution was cooled to 30° C. and treated with 23 ml of a 25% solution of sodium methoxide in methanol. This mixture was heated and refluxed for 1 hour. The slurry was cooled to 15° C. and treated with a solution of 30 ml of 6N hydrochloric acid in 350 ml of water. After stirring in an ice bath for 2 hours, the pale gray solid was filtered and dried; yield 30.8 g, melting point 214°–216° C. A sample crystallized from methanol melted at 218°–220° C.

(C)

3-Carboxy-1,3,4,5-tetrahydro-4-(methoxyphenyl)-6-(trifluoromethyl)-2H-1-benzazepin-2-one To a stirred warm solution of 58.0 g (0.88 mol) of potassium hydroxide (85%) in 500 ml of methanol was added portionwise 81.7 g (0.21 mol) of 1,3,4,5-tetrahydro-3-(methoxycarbonyl)-4-(methoxyphenyl)-6-(trifluoromethyl)-2H-1-benzazepin-2-one - most of the solid dissolved. The mixture was diluted with 100 ml of dioxane and the resulting solution was refluxed for 6 hours. After standing overnight at room temperature, about 50% of the solvent was removed on a rotary evaporator and the residue was diluted with 4 liters of cold water. The insoluble material was filtered and dried (10 g) and the filtrate was cooled and treated portionwise with 270 ml of acetic acid to give a colorless granular solid. The latter was filtered, washed with cold water and dried in a desicator; yield 69.0 g, melting point 179°–181° C. (s. 128° C.).

(D)

(d-trans)-3-Carboxy-1,3,4,5-tetrahydro-4-(methoxyphenyl)-6-(trifluoromethyl)-2H-1-benzazepin-2-one, (−)-α-methylbenzylamine salt A mixture of 67.0 g (0.176 mol) of 3-carboxy-1,3,4,5-tetrahydro-4-(methoxyphenyl)-6-(trifluoromethyl)-2H-1-benzazepin-2-one and 1 liter of ethanol was warmed and the resulting solution (52° C.) was treated with a solution of 21.4 g (0.176 mol) of (−)-α-methylbenzylamine in 100 ml of ethanol. This solution was seeded and allowed to stand undisturbed for 24 hours at room temperature. The product separated as well-formed crystals on the walls of the flask. The mother liquor was decanted from the solid and the latter was suspended in 70 ml of ethanol, filtered and wshed with fresh ethanol to give 34.6 g of a colorless solid, melting point 156° C. (dec.); $[\alpha]_D -10.3°$ (c, 1% methanol).

(E)

(d-trans)-3-Carboxy-1,3,4,5-tetrahydro-4-(methoxyphenyl)-6-(trifluoromethyl)-2H-1-benzazepin-2-one (d-trans)-3-Carboxy-1,3,4,5-tetrahydro-4-(methoxyphenyl)-6-(trifluoromethyl)-2H-1-benzazepin-2-one, (−)-α-methylbenzylamine salt (34.0 g, 67.9 mmole) was stirred in dichloromethane (780 ml) and water (390 ml), and treated with 1N hydrochloric acid (78 ml). Methanol (195 ml) was added in increments to expedite solvation. After 2 clear layers were obtained (15–20 minutes), the organic layer was separated. The aqueous layer was extracted with dichloromethane (twice) and the combined organic layers were washed with water (200 ml). The organic layer was dried (magnesium sulfate) and concentrated. The residue was coevaporated with acetone (three times). Crude yield=27.1 g.

(F)

(d-trans)-1,3,4,5-Tetrahydro-3-(methoxycarbonyl)-4-(methoxyphenyl)-6-(trifluoromethyl)-2H-1-benzazepin-2-one (d-trans)-3-Carboxy-1,3,4,5-tetrahydro-4-(methoxyphenyl)-6-(trifluoromethyl)-2H-1-benzazepin-2-one (25.75 g; 67.87 mmole) was dissolved in acetone (200 ml), and 1,8-diazabicyclo[5.4.0]-undec-7-ene (10.54 g; 10.4 ml; 69.22 mmole; 1.01 eq; d=1.018) was added with stirring at room temperature. (After less than one minute, a white precipitate formed). Methyl iodide (43 ml; 96.3 g; sp. gr. 2.24–2.26; 678.7 mmole; 10 eq) was added and the mixture was heated at ~45° C. (After ~1 minute, the solution turned homogeneous and yellow). The mixture was allowed to stir for 15 minutes before concentrating it and partitioning the residue between chloroform and saturated potassium bisulfate. The aqueous phase was extracted with chloroform (four times), and the combined organics were dried (magnesium sulfate) and concentrated giving 51.74 g of a yellow viscous oil. A slightly yellow solid was obtained by co-evaporating the residue with ether. This material was preabsorbed onto 60–200 mesh silica gel and layered onto a silica gel packed (10 cm high) column. 1:1 Hexane:ethyl acetate was used to wash the product out of the column leaving baseline contamination at the origin. The filtrate was dried (magnesium sulfate), concentrated co-evaporated with ether (twice) and vacuum dried yielding 24.78 g of the title compound.

(G)

(d-trans)-1,3,4,5-Tetrahydro-3-(methoxycarbonyl)-1-(methoxymethyl)-4-(methoxyphenyl)-6-(trifluoromethyl)-2H-1-benzazepin-2-one Following the procedure of Example 5, Method I, part C, but utilizing (d-trans)-1,3,4,5-tetrahydro-3-(methoxycarbonyl)-4-(methoxyphenyl)-6-(trifluoromethyl)-2H-1-benzazepin-2-one (10.87 g; 27.63 mmole); freshly distilled methoxymethyl bromide (2.5 ml; 3.8 g; 30.39 mole; d=1.531; 1.1 eq.), prewashed (ether) sodium hydride (0.86 g; 35.92 mmole; 1.3 eq.), and dimethylformamide (110 ml) yielded the crude title compound (15.83 g). The crude material was flashed using a gradient of 10% ethyl acetate/hexane to 20% ethyl acetate/hexane. The yield of pure product was 4.23 g. An additional 4.44 g of starting material product mixture, and 1.98 g of pure recovered starting material were also obtained.

(H)

(d)-1,3,4,5-Tetrahydro-3-(methoxycarbonyl)-1-(methoxymethl)-4-(methoxyphenyl)-3-(2-propenyl)-6-(trifluoromethyl)-2H-1-benzazepin-2-one Following the procedure of Example 5, Method I, part D, but utilizing (d-trans)-1,3,4,5-tetrahydro-3-(methoxycarbonyl)-1-(methoxymethyl)-4-(methoxyphenyl)-6-(trifluoromethyl)-2H-1-benzazepin-2-one (10.39 g; 23.7 mmole), allyl bromide (4.1 ml; 5.75 g; 47.5 mmole; d=1.398; 2 eq., 50% sodium hydride (2.28 g; 47.5 mmole; 2 eq.) and dry dimethylformamide (110 ml) yielded the crude title compound (17.84 g) as a yellow oil. The oil solidified on coevaporation with ether.

(I)

(d)-1,3,4,5-Tetrahydro-3-(methoxycarbonyl)-4-(methoxyphenyl)-3-(2-propenyl)-6-(trifluoromethyl)-2H-1-benzazepin-2-one Following the procedure of Example 5, Method I, part E, but utilizing (d)-1,3,4,5-tetrahydro-3-(methoxycarbonyl)-1-(methoxymethyl)-4-(methoxyphenyl)-3-(2-propenyl)-6-(trifluoromethyl)-2H-1-benzazepin-2-one (11.27 g; 23.62 mmole), methanol (240 ml), sulfuric acid (40 ml), dry lithium bromide (8.65 g; 99.6 mmole) yielded the crude title compound as a yellow oily residue. The residue was dissolved in ethyl acetate and suction filtered through a pad of silica gel. The clear, yellow filtrate was concentrated forming a light yellow semi-solid.

(J)

(d-cis)-1,3,4,5-Tetrahydro-4-(methoxyphenyl)-3-(2-propenyl)-6-(trifluoromethyl)-2H-1-benzazepin-2-one Following the procedure of Example 5, Method I, part F, but utilizing (d)-1,3,4,5-tetrahydro-3-(methoxycarbonyl)-4-(methoxyphenyl)-3-(2-propenyl)-6-(trifluoromethyl)-2H-1-benzazepin-2-one (10.20 g; 23.53 mmole), lithium iodide (12.60 g; 94.12 mmole; 4 eq.), pyridine (210 ml) and water (4 ml) yielded 8.95 g of the crude title compound.

(K)

(cis)-1-[2-(Dimethylamino)ethyl]-1,3,4,5-tetrahydro-4-(4-methoxyphenyl)-3-propyl-6-(trifluromethyl)-2H-1-benzazepin-2-one, monohydrochloride Following the procedure of Example 5, Method I, part G, but utilizing (d-cis)-1,3,4,5-tetrahydro-4-(methoxyphenyl)-3-(2-propenyl)-6-(trifluoromethyl)-2H-1-benzazepin-2-one (8.79 g; 23.42 mmole), potassium iodide,(catalytic amount), potassium bicarbonate (9.47 g; 93.68 mmole), methylethyl ketone (105 ml), 2.15 M N,N-dimethyl-2-chloroethylamine in toluene (27.2 ml; 58.55 mmole) yielded the crude title compound. Recrystallization (hexane) of the crude product followed by hexane trituration of the precipitate gave pure cis material which was dissolved in ether and treated with hydrochloric acid. The resulting hydrochloride salt was recrystallized from ethyl acetate to yield 3.55 g of the title compound, melting point 225°–227° C. (dec.), [α $_D$+96.7° (c=1, methanol).

Analysis Calc'd. for $C_{25}H_{29}F_3N_2O_2 \cdot HCl \cdot 1.8H_2O$: C, 58.28; H, 6.57; N, 5.43; Cl, 6.88; F, 11.06. Found:C, 58.25; H, 6.15; N, 5.39; Cl, 6.70; F, 11.00.

EXAMPLE 10

(d-cis)-1-[2-(Dimethylamino)ethyl]-1,3,4,5-tetrahydro-4-(4-methoxyphenyl)-3-ethyl-6-(trifluoromethyl)-2H-1-benzazepin-2-one, monohydrochloride

(A)

(d)-1,3,4,5-Tetrahydro-3-(methoxycarbonyl)-1-(methoxymethyl)-4-(methoxyphenyl)-3-ethyl-6-(trifluoromethyl)-2H-1-benzazepin-2-one To a suspension of 1.2 g of sodium hydride (25 mmole, 50% oil dispersion which was prewashed with ether) in 50 ml of dimethylformamide, cooled at 0°–5° C. in an ice water bath was added with stirring 5.2 g crude solid (d-trans)-1,3,4,5-tetrahydro-3-(methoxycarbonyl)-1-(methoxymethyl)-4-(methoxyphenyl)-6-(trifluoromethyl)-2H-1-benzazepin-2-one (see Example 9G) in small portions. The reaction mixture was stirred at 0°–5° for 20 minutes, whereupon 2 ml of iodoethane was added dropwise (25 mmole, 2 equivalents). The reaction mixture was allowed to stand at 0° C. to room temperature for 2 hours, whereupon excess hydride was destroyed by the careful addition of water. The reaction mixture was diluted with ether and washed with water. The combined aqueous layer was extracted once with ether. The ether layer was dried over anhydrous magnesium sulfate and concentrated under reduced pressure. The crude yellow residue was chromatographed on a silica gel column and eluted with 5–20% ethyl acetate in hexane to obtain 5.01 g of the title compound as an oil.

(B)

(d)-1,3,4,5-Tetrahydro-3-(methoxycarbonyl)-4-(methoxyphenyl)-3-ethyl-6-(trifluoromethyl)-2H-1-benzazepin-2-one To a solution of 4.85 g (10.7 mmole) of (d)-1,3,4,5-tetrahydro-3-(methoxycarbonyl)-1-(methoxymethyl)-4-(methoxyphenyl)-3-ethyl-6-(trifluoromethyl)-2H-1-benzazepin-2-one in 100 ml of methanol, cooled in an ice water bath was added dropwise 20 ml of concentrated sulfuric acid. To this solution was added 2.7 g of anhydrous lithium bromide. The cooling bath was removed and the reaction mixture was heated under reflux (bath temperature 80° C.). Heating was continued for 2½ hours, whereupon the reaction mixture was cooled (ice water bath) and diluted with water. A white precipitate was observed. Acid was carefully neutralized by the addition of solid sodium bicarbonate. The reaction mixture was extracted thoroughly with ethyl acetate (4 times). The combined ethyl acetate extract was washed with saturated brine solution, dried over anhydrous magnesium sulfate and concentrated under reduced pressure. The crude residue was chromatographed on a silica gel column and eluted with 20–50% ethyl acetate in hexane to obtain 4.36 g of white crystalline product; melting point 77°–81° C.

(C)

(d-cis)-1,3,4,5-Tetrahydro-4-(methoxyphenyl)-3-ethyl-6-(trifluoromethyl)-2H-1-benzazepin-1-one Lithium iodide (3.96 g, 29.6 mmole) was added to (d)-1,3,4,5-tetrahydro-3-(methoxycarbonyl)-4-(methoxyphenyl)-3-ethyl-6-(trifluoromethyl)-2H-1benzazepin-2-one (3.12 g, 7.4 mmole) in 40 ml of pyridine and 3 ml of water, and the mixure was refluxed at 133° C. for 4½ hours. Additional lithium iodide (1.00 g ) and dimethylformamide (10 ml) were added and the reflux was continued overnight. The mixture was cooled and partitioned between ether and 1N hydrochloric acid. The aqueous layer was extracted several times with ether, and the combined organic layers were dried (magnesium sulfate) and concentrated. The crude, dark oily residue was flash chromatographed (silica gel; 1–10% pyridine:hexane) giving 2.65 g of crude (d-cis)-1,3,4,5-tetrahydro-4-(methoxyphenyl)-3-ethyl-6-(trifluoromethyl)-2H-1-benzazepin-1-one (an approximately 80:20-cis:trans mixture was obtained).

(D)

(d-cis)-1-[2-(Dimethylamino)ethyl]-1,3,4,5-tetrahydro-4-(4-methoxyphenyl)-3-ethyl-6-(trifluoromethyl)-2H-1-benzazepin-2-one, monohydrochloride Prewashed (hexane) sodium hydride (0.26 g, 10.7 mmole) and (d-cis)-1,3,4,5-tetrahydro-4-(methoxyphenyl)-3-ethyl-6-(trifluoromethyl)-2H-1-benzazepin-1-one (2.60 g, 7.15 mmole) were stirred in 50 ml of dry dimethylformamide for 35 minutes. A 2.15M toluene solution of N,N-dimethyl-2-chloroethylamine (13.3 ml, 28.6 mmole) was then added, and the mixture was heated at 80° C. for 1½ hours with stirring. The reaction was quenched with 1N hydrochloric acid, made basic with 50% sodium hydroxide solution, and paritioned between ethyl acetate/water. The aqueous layer was extracted with ethyl acetate, and the combined organic layers were dried (magnesium sulfate) and concentrated. The free amine was recrystallized from hot hexane (3 times), dissolved into ethyl acetate and washed with 1N sodium bicarbonate. The ethyl acetate layer was dried (magnesium sulfate) and then treated with saturated hydrochloric acid in ether. The concentrated mixture was vacuum dried overnight giving 0.52 g of white solid product, 5 melting point 162°–164° C., $[\alpha]_D + 112°$. (The mother liquor contained additional product).

Analysis Calc'd. for $C_{24}H_{29}N_2O_2F_3 \cdot HCl \cdot 0.95H_2O$: C., 59.07; H, 6.59; N, 5.74; F, 11.67; Cl, 7.26. Found: C, 59.07; H, 6.71; N, 5.76; F, 11.89; Cl, 7.51.

EXAMPLE 11

(d-cis)-1-[2-(Dimethylamino)ethyl]-1,3,4,5-tetrahydro-4-(4-methoxyphenyl)-3-methyl-6-(trifluoromethyl)-2H-1-benzazepin-2-one, monohydrochloride (A)

(d)-1,3,4,5-Tetrahydro-3-(methoxycarbonyl)-1-(methoxymethyl)-4-(methoxyphenyl)-3-methyl-6-(trifluoromethyl)-2H-1-benzazepin-2-one To a suspension of 1.2 g of sodium hydride (25 mmole) in 50 ml of dry dimethylformamide, cooled in an ice water bath was added with stirring 5.2 g of (d-trans)-1,3,4,5-tetrahydro-3-(methoxycarbonyl)-1-(methoxymethyl)-4-(methoxyphenyl)-6-(trifluoromethyl)-2H-1-benzazepin-2-one (12 mmole, crude; see Example 9G) in small portions. After stirring for 20 minutes at 0°–5° C., 1.6 ml of iodomethane (25 mmole) was added rapidly. The reaction mixture was allowed to stand at 0° C. to room temperature for 3 hours, whereupon excess hydride was destroyed by careful addition of water. The reaction mixture was diluted with ether and washed with water. The aqueous layer was extracted with ether. The combined ether extract was dried over anhydrous magnesium sulfate and concentrated under reduced pressure. The crude yellow oil was chromatographed on a silica gel column and eluted with 5–20% ethyl acetate in hexane to obtain 4.68 g of the title compound.

(B)

(d)-1,3,4,5-Tetrahydro-3-(methoxycarbonyl)-4-(methoxyphenyl)-3-methyl-6-(trifluoromethyl)-2H-1-benzazepin-2-one To a solution of 4.37 g of (d)-1,3,4,5-tetrahydro-3-(methoxycarbonyl)-1-(methoxymethyl)-4-(methoxyphenyl)-3-methyl-6-(trifluoromethyl)-2H-1-benzazepin-2-one (9.7 mmole) in 100 ml of methanol, cooled in an ice water bath was added 2.7 g of anhydrous lithium bromide, followed by 20 ml of concentrated sulfuric acid dropwise. The cooling bath was removed and the reaction mixture was heated under reflux (bath temperature 80°–85° C.) for 4 hours. The reaction mixture was cooled and diluted with ice cold water. Acid was neutralized by the careful addition of solid sodium bicarbonate followed by extraction with ethyl acetate. The combined organic extract was washed once with brine and dried over anhydrous magnesium sulfate. Concentration under reduced pressure left a yellow oily residue which was chromatographed on a silica gel column. Elution with 5–25% ethyl acetate in hexane afforded 1.6 g of the desired white crystalline product, melting point 71°–76° C.

(C)

(d-cis)-1,3,4,5-Tetrahydro-4-(methoxyphenyl)-3-methyl-6-(trifluoromethyl)-2H-1-benzazepin-2-one To a solution of 1.5 g (d)-1,3,4,5-tetrahydro-3-(methoxycarbonyl)-4(methoxyphenyl)-3-methyl-6-(trifluoromethyl)-2H-1-benzazepin-2-one (4 mmole) in 12 ml of dimethylformamide was added with stirring 2 g of anhydrous lithium bromide and 920 mg of p-aminothiophenol (~8 mmole). The reaction mixture was placed on an oil bath and heted to 135° C. under an argon atmosphere for 5 hours. It wad cooled and diluted with ice water. The reaction mixture was extracted with ether (3 times) and the combined ether extract was washed with water, 1N aqueous hydrochloric acid solution (2 times) and finally with saturated sodium chloride solution. The ether layer was dried over anhydrous magnesium sulfate and concentrated under reaction pressure to obtain 1.3 g of a light yellow viscous oil. NMR spectrum of the crude product indicated the cis/-trans ratio to be approximately 20:1.

(D)
(d-cis)-1-[2-(Dimethylamino)ethyl]-1,3,4,5-tetrahydro-4-(4-methoxyphenyl)-3-methyl-6-(trifluoromethyl)-2H-1-benzazepin-2-one, monohydrochloride To a slurry of washed (ether) sodium hydride (0.13 g; 5.58 mmole) in dry dimethylformamide (15 ml) was added (d-cis)-1,3,4,5-tetrahydro-4-(methoxyphenyl)-3-methyl-6-(trifluromethyl)-2H-1-benzazepin-2-one (1.27 g; 3.64 mmole). The mixture was stirred at room temperature for 35 minutes before a 2.15 M toluene solution of N,N-dimethyl-2-chloroethylamine (5.2 ml; 11.2 mmole) was added, and the solution was heated at 80° C. for 6 hours. The reaction was quenched with 1N hydrochloric acid, made basic with 50% sodium hydroxide solution, extracted with ethyl acetate (3 times), and dried over magnesium sulfate. The concentrated residue was coevaporated with hexane (3 times) and placed under vacuum overnight. The crude material was purified by preparative plate chromatography (silica gel, 5% methanol:dichloromethane developed 3 times), dissolved in ethyl acetate, washed with 1N sodium bicarbonate, and dried (magnesium sulfate). The solution was treated with ethereal hydrochloric acid solution, concentrated, coevaporated with ether (4 times), and dried in vacuo giving 870 mg of white solid product, melting point 146°–148° C., $[\alpha]_D +100.4°$ (methanol).

Analysis Calc'd. for $C_{23}H_{27}N_2O_2F_3.HCl .1.91H_2O$: C, 56.23; H, 6.53; N, 5.70; F, 11.60; Cl, 7.22. Found: C, 56.44; H, 6.69; N, 5.83; F, 11.62; Cl, 7.04.

EXAMPLE 12

(cis)-1,3,4,5-Tetrahydro-4-(4-methoxyphenyl)-3-methyl-1-[2-[methyl(phenylmethyl)amino]ethyl-6-(trifluoromethyl)-2H-1-benzazepin-2-one, monohydrochloride Under argon, a stirred solution of 3.0 g (8.6 mmol) of (cis)-1,3,4,5-tetrahydro-4-(4-methoxyphenyl)-3-methyl-6-(trifluoromethyl)-2H-1-benazepin-2-one (see Example 11C) in 90 ml of dimethylformamide was treated with 0.39 g (9.75 mmol) of 60% sodium hydride and stirred for 1 hour. 6.1 ml (12.9 mmol) of a 2.1 N toluene solution of N-benzyl-N-methylaminoethyl chloride (released into toluene from the hydrochloride salt with aqueous potassium carbonate) was added and the mixture was heated at 75°–83° C. (oil bath temperature) for 2 hours. TLC (90:10 dichloromethane-methanol and 18:1:1 dichloromethane-methanol-acetic acid) showed the reaction to be complete.

After standing overnight, the bulk of the dimethylformamide was removed on a rotary evaporator at 0.2 mm of Hg, and the residue was shaken with 80 ml of ethyl acetate and 100 ml of water containing 18 ml of 1N hydrochloric acid. The organic layer was dried, evaporated and the residue pump-dried to give 4.8 g of an amorphous solid. After standing overnight, the material was stirred in 500 ml of 1:1 ether-ethyl acetate and 100 ml of water until two clear layers were obtained. These were separated, the organic phase washed with 25 ml of water and brine, dried and evaporated to give 4.37 g of a sticky foam. This residue in 150 ml of methanol was then treated with 1.9 ml of 5N ethanolic hydrogen chloride and the solvent evaporated. The sticky residue was rubbed under ether and the evaporation repeated. The partially solid residue was rubbed under fresh ether and cooled for 2 hours to give a nearly colorless solid which was filtered under argon, washed with ether, and dried in vacuo; yield, 4.25 g; melting point 80°–83° C. (foaming); sintering at 76° C.

Analysis Calc'd. for $C_{29}H_{31}F_3N_2O_2.HCl.0.5H_2O$: C, 64.26; H, 6.14; N, 5.17; Cl, 6.54. Found: C, 64.40; H, 6.32; N, 5.06; Cl, 6.65.

EXAMPLE 13

(cis)-1,3,4,5-Tetrahydro-4-(4-methoxyphenyl)-3-methyl-1-[2-(methylamino)ethyl]-6-(trifluoromethyl)-2H-1-benzazepin-2-one, monohydrochloride A solution of (cis)-1,3,4,5-tetrahydro-4-(4-methoxyphenyl)-3-methyl-1-[2-[methyl(phenylmethyl)amino]ethyl-6-(trifluoromethyl)-2H-1-benzazepin-2-one, monohydrochloride (3.0 g; 5.6 mmole; see Example 12) in 100 ml of acetic acid was treated with 2.3 g of 10% palladium on charcoal and shaken on the Parr hydrogenator for 4 hours at 50 psi. The catalyst was filtered off under argon, washed with acetic acid, and the acetic acid removed on a rotary evaporator at 0.2 mm (last traces azeotroped with toluene) and the syrupy residue rubbed under ether (gradually solidified). The evaporation was repeated and the colorless solid pump-dried; yield, 2.3 g. Following crystallization (of 2.2 g) from 15 ml of hot methanol—30 ml of ether, the solid weighed 1.88 g; melting point 246°–248° C. (dec.); sintering at 243° C.

Analysis Calc'd. for $C_{22}H_{25}F_3N_2O_2.HCl.0.5H_2O$: C, 58.47; H, 6.02; N, 6.20; Cl, 8.01. Found: C, 58.50; H, 5.79; N, 6.22; Cl, 8.18.

EXAMPLE 14

(cis)-1-[2-(Diisopropylamino)ethyl]-1,3,4,5-tetrahydro-4-(4-methoxyphenyl)-3-methyl-(6-trifluoromethyl)-2H-1-benzazein-2-one, monohydrochloride The reaction of 3.0 g (8.6 mmol) of (cis)-1,3,4,5-tetrahydro-4-(4-methoxyphenyl)-3-methyl-6-trifluoromethyl)-2H-1-benzazepin-2-one (see Example 11C) in 90 ml of dimethylformamide with 0.39 g (9.7 mmol) of sodium hydride (60%) and 6.1 ml (19.2 mmol) of 2.1N 2-diisopropylaminoethyl chloride in toluene following the procedure of Example 12 gave 4.25 g of product. After crystallization from 25 ml of isopropanol, the colorless solid weighed 3.35 g, melting point 204°–206° C.

A solution of 3.25 g of this base in 50 ml of methanol was treated with 1.4 ml of 5.1N hydrogen chloride in ethanol. After removal of the solvent, the syrupy residue was treated with ether and the solvent removed under reduced pressure to give 3.77 g of a colorless solid, melting point 81°–84° C.

Analysis Calc'd. for $C_{27}H_{35}F_3N_2O_2.HCl.0.5H_2O$: C, 62.11; H, 7.13; N, 5.37; Cl, 6.79. Found: C, 62.12; H, 7.33; N, 5.27; Cl, 6.83.

EXAMPLE 15

(cis)-1-2-(Dimethylamino)ethyl]-1,3,4,5-tetrahydro-3-methyl-4-(4-methoxyphenyl)-2H-1-benzazepin-2-one, monohydrochloride

(A)

[2-(2-Nitrophenyl)-1-(4-methyoxyphenyl)ethyl]-propanedioic acid, dimethyl ester

After preparing a slurry of sodium hydride (3.6 g, 150 mmol; obtained by removing the oil from 6.0 g of 60% dispersion with diethyl ether) in 375 ml of dimethylformamide, 25.0 g (100 mmol) of dimethyl 4-methoxybenzylidine malonate was added and allowed to dissolve. To this mixture, a solution of 2-nitrotoluene (15.1 g, 110 mmol) in 25 ml of dimethylformamide was added dropwise over an approximately 1 hour period. The reaction was then allowed to stir overnight and subsequently judged complete by tlc (4:1 hexane-ethyl acetate, disappearance of starting malonate). The reaction was quenched by the addition of 20 ml of acetic acid in 50 ml of methanol followed by the addition of 1 L of water. The mixture was then extracted with ethyl acetate (3 times, 250 ml) and the combined organic extracts were then washed successively with 1N hydrochloric acid, saturated potassium bicarbonate, and brine. The dark organic solution was then dried over magnesium sulfate and concentrated in vacuo to a dark red-brown oil. The material was dissolved in warm methanol and allowed to cool to room temperature. After seeding with known product, the mixture was allowed to crystallize overnight and the product collected by filtration. This material was recrystallized from methanol to yield 22.2 g of the desired product. The mother liquors from both crystallizations were combined and concentrated in vacuo. The residue was then dissolved in 1:1 hexane-ethyl acetate and passed through a 50 cm × 35 cm pad of silica gel to remove much of the dark, polar byproducts. Concentration and recrystallization of the residue from methanol afforded an additional 6.4 g of material for a combined yield of 28.6 g of tan crystalline product which was homogeneous by tlc analysis; melting point 73°–75° C.

(B)

α-Methyl-[2-(2-nitrophenyl)-1-(4-methoxyphenyl)-ethyl]propanedioic acid, dimethyl ester To a solution of [2-(2-nitrophenyl)-1-(4-methoxyphenyl)ethyl]propanedioic acid, dimethyl ester (4.0 g, 10.33 mmol) in 19 ml of dimethylformamide (0° C., argon) was added sodium hydride dispersion (0.5 g, 12.40 mmol). Stirring at 0° C. was continued for 5 minutes. Iodomethane was added (3.21 ml, 51.63 mmol) and the reaction was carried out at room temperature for 2 hours, 15 minutes. Ethyl acetate and 1M hydrochloric acid were added, the aqueous layer was washed with ethyl acetate, the combined ethyl acetate layers were washed with 1M hydrochloric acid (two times), saturated aqueous potassium carbonate solution, brine, dried over magnesium sulfate and evaporated in vacuo to yield 4.61 g of a viscous yellow oil. The oil was washed with several portions of hexane. Recrystallization of the residue (3.88 g of a sticky yellow solid) from methanol two times, (1 crop each) yielded 2.69 g of a white crystalline solid, melting point 82°–84° C.

(C)

α-Methyl-[2-(2-aminophenyl)-1-(4-methoxyphenyl)ethyl]propanedioic acid, dimethyl ester A solution of α-methyl-[2-(2-nitrophenyl)-1-(4-methoxyphenyl)ethyl]propanedioic acid, dimethyl ester (2.47 g, 6.38 mmol) in 24 ml of trifluoroacetic acid was catalytically hydrogenated (42 psi, 0.25 g of 10% palladium on charcoal) for 1½ hours. The reaction suspension was filtered through a pad of Celite and concentrated in vacuo to yield a viscous brown oil. The crude product was dissolved in ethyl acetate and washed several times with saturated aqueous potassium carbonate solution. Evaporation of the ethyl acetate layer in vacuo yielded 2.27 g of a light tan solid. Recrystallization from methanol (3 crops) yielded 1.82 g of an off-white solid, melting point 165°–167° C.

(D)

1,3,4,5-Tetrahydro-3-(methoxycarbonyl)-4-(4-methoxphenyl)-3-methyl-2H-1-benzazepin-2-one A solution of α-methyl-[2-(2-aminophenyl)-1-(4-methoxyphenyl)ethyl]propanedioic acid, dimethyl ester (1.73 g, 4.66 mmol) with sodium methoxide (5.32 ml, 23.28 mmol of a 25 weight percent solution in methanol) in 12 ml of methanol/3 ml of dimethylformamide was refluxed under argon for 4 days. The reaction had still not gone to completion. 1M Hydrochloric acid was slowly added (0° C. ice bath) and stirring was continued for 10 minutes. The crude product was collected by filtration and washed with 90/10 water/methanol. Yield: 1.77 g of a light tan solid. Recrystallization from ethyl acetate/hexane (2 crops) yielded 0.74 g of a white solid, melting point 198°–200.5° C.

(E)

(cis)-1,3,4,5-Tetrahydro-4-(4-methoxyphenyl)-3-methyl-2H-1-benzazepin-2-one

A solution of 1,3,4,5-tetrahydro-3-(methoxycarbonyl)-4-(4-methoxphenyl)-3-methyl-2H-1-benzazepin-2-one (0.67 g, 1.97 mmol), lithium bromide (0.98 g 11.25 mmol), and α-aminothiophenol (0.49 g, 3.94 mmol) in 60 ml of dimethylformamide (argon) was heated to 137° C. (oil bath temperature) for 5 hours. After the reaction mixture was cooled to room temperature, 1M hydrochloric acid and ethyl acetate were added. The aqueous layer was washed with ethyl acetate, the combined ethyl acetate layers were washed with 1M hydrochloric acid (3 times), saturated aqueous potassium carbonate solution (2 times), brine, dried over magnesium sulfate and evaporated in vacuo to yield 0.53 g of a white, somewhat sticky solid. The crude product was used for the next step without purification.

(F)

(cis)-1-[2-(Dimethylamino)ethyl]-1,3,4,5-tetrahydro-3-methyl-4-(4-methoxyphenyl)-2H-1-benzazepin-2-one, monohydrochloride A solution of (cis)-1,3,4,5-tetrahydro-4-(4-methoxyphenyl)-3-methyl-2H-1-benzazepin-2-one (0.37 g, 1.32 mmol) in 13 ml of dry dimethylformamide was treated with sodium hydride (0.035 g, 1.45 mmol, room temperature, argon) and stirring at room temperature was continued for one-half hour. N,N-Dimethyl-2-chloroethylamine (0.92 ml of a 2.15M solution in toluene 1.97 mmol) was introduced and the reaction was carried out for 3 hours (85° C. oil bath). TLC indicated that reaction progress had stopped after 1½ hours. More sodium hydride (0.02 g, 0.83 mmol) was added (room temperature) followed by more N,N-dimethyl-2-chloroethylamine solution (0.46 ml, 0.99 mmol). The reaction was continued at 85° C. (oil bath temperature) for 3½ hours. Dimethylformamide was removed in vacuo. Ethyl acetate and water were added, the water layer was washed with ethyl acetate, the combined ethyl acetate layers were washed with water (2 times), brine, dried over sodium sulfate and evaporated in vacuo to yield 0.42 g of a yellow oil. Acidification with saturated hydrogen chloride/ether solution followed by evaporation in vacuo and subsequent trituration with ether (1 crop) yielded 0.37 g of an off-white solid. TLC of the mother liquor revealed the presence of unconsumed starting material. Recrystallization from ethyl acetate/methanol (2 crops) yielded 0.22 g of an off-white solid, melting point 211°–216° C., dec. (foaming).

Analysis Calc'd. for $C_{22}H_{28}N_2O_2 \cdot HCl \cdot 0.44H_2O$: C, 66.58; H, 7.59; N, 7.06; Cl, 8.93. Found: C, 66.28; H, 7.30; N, 6.92; Cl, 9.28.

EXAMPLE 16

(cis)-1-[2-(Dimethylamino)ethyl]-1,3,4,5-tetrahydro-4-(4-methoxyphenyl)-3-(2-propenyl)-2H-1-benzazepin-2-one, monohydrochloride

(A)

α-(2-Propenyl)-[2-(2-nitrophenyl)-1-(4-methoxyphenyl)ethyl]propanedioic acid, dimethyl ester A solution of [2-(2-nitrophenyl)-1-(4-methoxyphenyl)ethyl]propanedioic acid, dimethyl ester (10 g, 25.81 mmol; see Example 15A) in 51 ml of dry dimethylformamide (0° C., argon) was treated with sodium hydride (6.19 g, 154.86 mmol of a 60% mineral oil dispersion); stirring at 0° C. was continued for 20 minutes. Allyl bromide* (11.17 ml, 129.05 mmol) was added and the reaction was carried out at room temperature for 1 hour, 10 minutes. The reaction was quenched by the slow addition of 1M hydrochloric acid (0° C. ice bath) followed by ethyl acetate. The aqueous layer was washed with ethyl acetate, the combined ethyl acetate layers were washed with 1M hydrochloric acid (3 times), saturated aqueous potassium carbonate solution (2 times), brine, dried over magnesium sulfate and evaporated in vacuo. The crude product was dissolved in dichloromethane and adsorbed onto Celite and filtered through a pad of silica gel (240-400 mesh, hexane, followed by 75/25 hexane/ethyl acetate). Evaporation in vacuo yielded 10.66 g of a viscous yellow-orange oil.
*Allyl bromide was purged of HBr by standing several minutes over basic alumina.

(B)

α-(2-Propenyl)-[2-(2-aminophenyl)-1-(4-methoxyphenyl)ethyl]propanedioic acid, dimethyl ester To a solution of prepulverized stannous chloride dihydrate (23.82 g, 105.59 mmol) in methanol/concentrated sulfuric acid (318 ml/31.8 ml) at room temperature under a stream of nitrogen was added α-(2-propenyl)-[2-(2-nitrophenyl)--1-(4-methoxyphenyl)ethyl]propanedioic acid, dimethyl ester as a solution in 151 ml of methanol. The reaction was run at 40°–58° C. (water bath temperature) for several hours, and then at room temperature overnight. The reaction was quenched by addition of the following reagents in the order specified: Celite, ethyl acetate (389 ml), saturated aqueous potassium carbonate solution (150 ml), and potassium carbonate (101 g), followed by agitation for about 15 minutes. Filtration through two Celite pads (once with a C porosity fritted glass funnel then a D porosity fritted glass funnel) followed by evaporation of the solvents in vacuo yielded a tan oil. Trituration from methanol/water (1 crop) yielded an off-white solid which was recrystallized from methanol (2 crops) to yield 6.87 g of an off-white crystalline solid, melting point 117°–118° C.

(C)

1,3,4,5-Tetrahydro-3-(methoxycarbonyl)-4-(4methoxyphenyl)-3-(2-propenyl)-2H-1-benzazepin-2-one A suspension of α-(2-propenyl)-[2-(2-aminophenyl)-1-(4-methoxyphenyl)ethyl]propanedioic acid, dimethyl ester (6.87 g, 17.28 mmol) in 44 ml of methanol with sodium methoxide solution (29.63 ml of a 25 weight percent solution, 129.6 mmol) was refluxed under argon overnight. Although the reaction mixture was nearly homogeneous under reflux, the reaction had not gone to completion (by TLC). After cooling to room temperature, 1M hydrochloric acid was added in several increments (total reaction volume was 200 ml). The crude product was collected by filtration, washed with 90/10 water/methanol, and recrystallized from methanol/water (2 crops) to yield 3.65 g of a white crystalline solid, melting point 175°–176.5° C.

(D)

(cis)-1,3,4,5-Tetrahydro-4-(4-methoxyphenyl)-3-(2-propenyl)-2H-1-benzazepin-2-one A solution of 1,3,4,5-tetrahydro-3-(methoxycarbonyl)-4-(4-methoxyphenyl)-3-(2-propenyl)-2H-1-benzazepin-2-one (4.56 g, 12.48 mmol), lithium bromide (6.18 g, 71.13 mmol) and α-aminothiophenol (3.12 g, 24.96 mmol) in 38 ml of dry dimethylformamide was heated to 137° C. (oil bath temperature) under argon for 5½ hours. The reaction mixture was cooled to room temperature and diluted with water (250 ml total volume). The precipitate was collected by filtration, rinsed with 1M hydrochloric acid, saturated aqueous potassium carbonate solution, water, and dried in vacuo with phosphorous pentoxide to give 3.5 g of a white solid. Recrystallization from methanol (3 crops) yielded 3.03 g of white needles, melting point 169°–171° C.

(E)

(cis)-1-[2-(Dimethylamino)ethyl]-1,3,4,5-tetrahydro-4-(4-methoxyphenyl)-3-(2-propenyl)-2H-1-benzazepin-2-one, monohydrochloride Following the procedure of Example 15F, but substituting (cis)-1,3,4,5-tetrahydro-4-(4-methoxyphenyl)-3-(2-propenyl)-2H-1-benzazepin-2-one for (cis)-1,3,4,5-tetrahydro-4-(4-methoxyphenyl)-3-methyl-2H-1-benzazepin-2-one, yielded 3.57 g of crude product as a tan oil. The oil was dissolved in 10 ml of ethyl acetate, treated with saturated ether-hydrochloric acid solution, evaporated in vacuo (coevaporated twice with ether) and triturated with ether/ethyl acetate (75 ml/25 ml, 1 crop) to yield 3.10 g of an off-white solid, melting point 154°–157° C. (dec.).

Analysis Calc'd. for $C_{24}H_{30}N_2O_2 \cdot HCl \cdot 0.35H_2O$: C, 68.42; H, 7.58; N, 6.65; Cl, 8.42. Found: C, 68.12; H, 7.44; N, 6.63; Cl, 8.78.

EXAMPLE 17

(cis)-1-[2-(Dimethylamino)ethyl]-1,3,4,5-tetrahydro-4-(4-methoxyphenyl)-3-propyl-2H-1-benzazepin-2-one, monohydrochloride A solution of (cis)-1-[2-(dimethylamino)ethyl]-1,3,4,5-tetrahydro-4-(4-methoxyphenyl)-3-(2-propenyl)-2H-1-benzazepin-2-one, monohydrochloride (1.5 g, 3.62 mmol; see Example 16) containing a 10% palladium on charcoal suspension (0.15 g, 10% b/w) was hydrogenated overnight at 1 atmosphere. The suspension was filtered through a Celite pad and evaporated in vacuo to yield 1.47 g of a white solid, melting point 178°–180° C., dec.

Analysis Calc'd. for $C_{24}H_{33}N_2O_2 \cdot HCl \cdot 0.38H_2O$: C, 68.02; H, 8.03; N, 6.61; Cl, 8.37. Found: C, 67.81; H, 8.05; N, 6.60; Cl, 8.61.

EXAMPLE 18

(d-cis)-1-[2-(Dimethylamino)ethyl]-1,3,4,5-tetrahydro-4-(4-methoxyphenyl)-3-(phenylmethyl)-6-(trifluoromethyl)-2H-1-benzazepin-2-one, fumarate (1:1) salt

(A)

(d)-1,3,4,5-Tetrahydro-3-(methoxycarbonyl)-1-(methoxymethyl)-4-(4-methoxyphenyl)-3-(2-phenylmethyl)-6-(trifluoromethyl)-2H-1-benzazepin-2-one To a suspension of 1.2 g of sodium hydride (25 mmol, washed with ether several times to remove mineral oil) in 50 ml of dry dimethylformamide, cooled in an ice water bath was added with stirring 5.2 g of crude solid (d-trans)-1,3,4,5-tetrahydro-3-(methoxycarbonyl)-1-(methoxymethyl)-4-(methoxyphenyl)-6-(trifluoromethyl)-2H-1-benzazepin-2-one (see Example 9G) in small portions. After stirring at 0°–5° C. for 20 minutes, 3 ml of benzyl bromide (25 mmole, 2 equivalents) was added rapidly. The reaction mixture was allowed to stand at 0° C. to greater than room temperature for 3 hours, whereupon excess hydride was destroyed by the addition of water. The reaction mixture was diluted with ether and washed with water several times. The combined aqueous layer was extracted with ether once. The combined ether extract was dried over anhydrous magnesium sulfate and concentrated to leave a yellow oily residue. The crude product was chromatographed on a silica gel column and eluted with 5–20% ethyl acetate in hexane to obtain 5.37 g of white crystalline product.

(B)

(d)-1,3,4,5-Tetrahydro-3-(methoxycarbonyl)-4-(4-methoxyphenyl)-3-(2-phenylmethyl)-6-(trifluoromethyl)-2H-1-benzazepin-2-one To a solution of 5.37 g of (d)-1,3,4,5-tetrahydro-3-(methoxycarbonyl)-1-(methoxymethyl)-4-(4-methoxyphenyl)-3-(2-phenylmethyl)-6-(trifluoromethyl)-2H-1-benzazepin-2-one (10 mmole) in 100 ml of methanol, cooled in an ice water bath was added 2.7 g of anhydrous lithium bromide followed by 20 ml of concentrated sulfuric acid dropwise. The cooling bath was removed and the reaction mixture was heated under reflux (bath temperature 80°–85° C.) for 2½ hours. The reaction mixture was cooled and diluted with ice water. A white precipitate immediately formed upon addition of water. Sulfuric acid was neutralized by careful addition of solid sodium bicarbonate, and the reaction mixture was extracted with ethyl acetate (4 times). The combined ethyl acetate extract was washed with brine, dried over anhydrous magnesium sulfate and concentrated. The crude residue was chromatographed on a silica gel column and eluted with 10–30% ethyl acetate in hexane to obtain 5.1 g of white crystalline product, melting point 97°–100° C.

(C)

(d)-1,3,4,5-Tetrahydro-4-(4-methoxyphenyl)-3-(2-phenylmethyl)-6-(trifluoromethyl)-2H-1-benzazepin-2-one (d)-1,3,4,5-Tetrahydro-3-(methoxycarbonyl)-4-(4-methoxyphenyl)-3-(2-phenylmethyl)-6-(trifluoromethyl)-2H-1-benzazepin-2-one (3.00 g; 6.21 mmole), and lithium iodide (4.16 g; 31.05 mmole) in dimethylformamide (35 ml) and water (2 drops) were heated at ~130° C. for 6 hours. The mixture was cooled, dissolved in ether, washed with sodium bisulfite (2 times), dried (magnesium sulfate), concentrated and vacuum-dried overnight, giving 2.53 g of beige solid product. This crude material was flashed (silica gel/3% to 10% pyridine:hexane) yielding 1.47 g of ~2:1-cis:trans (d)-1,3,4,5-tetrahydro-4-(4-methoxyphenyl)-3-(2-phenylmethyl)-6-(trifluoromethyl)-2H-1-benzazepin-2-one.

(D)

(d-cis)-1-[2-(Dimethylamino)ethyl]-1,3,4,5-tetrahydro-4-(4-methoxyphenyl)-3-(phenylmethyl)-6-(trifluoromethyl)-2H-1-benzazepin-2-one, fumarate (1:1) salt, (d)-1,3,4,5-Tetrahydro-4-(4-methoxyphenyl)-3-(2-phenylmethyl)-6-(trifluoromethyl)-2H-1-benzazepin-2-one (1.21 g; 2.84 mmole) was dissolved completely in refluxing methyl ethyl ketone (15 ml) under argon. Potassium carbonate (1.14 g, 11.4 mmole; 4 equivalents) was added to the solution followed by dimethylformamide (7 ml) maintaining the oil bath temperature at 85°–90° C. After stirring for 15 minutes, a 2.15 M toluene solution of N,N-dimethyl-2-chloroethylamine (2.65 ml; 5.69 mmole; 2 equivalents) was added, and heating was continued for 5 hours. The mixture was cooled, diluted with ethyl acetate, washed with water and 1N sodium bicarbonate, dried (magnesium sulfate), and concentrated. The crude light yellow free amine product weighed 1.28 g. This material was triturated in methanol and than recrystallized from methanol giving 0.45 g of pure cis free amine product, melting point 174.0°–175.0° C. This material was dissolved in warm methanol and an equivalent of fumarate was added with stirring. The concentrated mixture was vaccum-dried overnight leaving 530 mg of white solid, (d-cis)-1-[2-(dimethylamino)ethyl]-1,3,4,5-tetrahydro-4-(4-methoxyphenyl)-3-(phenylmethyl)-6-(trifluoromethyl)-2H-1-benzazepin-2-one, fumarate (1:1) salt, melting point 155°–159° C., $[\alpha]_D +55.2$ (c=1, methanol).

Analysis Calc'd. for $C_{29}H_{31}N_2F_3O_2$ (free amine): C, 70.15; H, 6.29; N, 5.64; F, 11.47. Found: C, 69.99; H, 6.63; N, 5.85; F, 11.58.

Analysis Calc'd. for $C_{33}H_{35}N_2F_3O_6 \cdot 0.42H_2O$ (fumarate salt): C, 63.91; H, 5.83; N, 4.52; F, 9.19. Found: C, 63.91; H, 5.77; N, 4.38; F, 9.55.

EXAMPLE 19

(cis)-6-Chloro-1-[2-(dimethylamino)ethyl]-3-ethyl-1,3,4,5-tetrahydro-4-(4-methoxyphenyl)-2H-1-benzazepin-2-one, fumarate (1:1) salt (A) [2-(5-Chloro-2-nitrophenyl)-1-(4-methoxyphenyl) ethyl]propanedioic acid, dimethyl ester To a 3 liter three-necked flask equipped with a mechanical stirrer, thermometer, pressure-equalized addition funnel, and argon purge were added dimethyl 4-methoxybenzylidene malonate (20.00 g, 0.0799 mole) and dry dimethylformamide (89 ml). The stirred solution was treated with prewashed (ether, 3 times), 50% sodium hydride (2.49 g, 0.104 mole). To this grey mixture was added 2-chloro-6-nitrotoluene (13.71 g, 0.0799 mole) in dimethylformamide (20 ml) dropwise and with stirring. The mixture was heated at 60° C. for 1 hour, and then cooled to room temperature. Ether was added and the solution was washed with water. The water layer was extracted with ether (2 times), and the organic extracts were combined and set aside for crystallization for 2 days. The huge prisms formed were collected by suction filtration, rinsed with ether (2 times) and vacuum dried, yielding 16.49 g of product, melting point 117°–120° C. Additional product was present in the mother liquor.

(B)
α-Ethyl-[2-(5-chloro-2-nitrophenyl)-1-(4-methoxyphenyl) ethyl]propanedioic acid, dimethyl ester

[2-(5-Chloro-2-nitrophenyl)-1-(4-methoxyphenyl)ethyl]propanedioic acid, dimethyl ester (15.29 g, 36.25 mmole) was dissolved in dry dimethylformamide (100 ml) under argon. Prewashed (ether, 3 times), 50% sodium hydride (1.04 g, 43.3 mmole) was added with stirring. (The mixture turned from yellow to a dark red color). Stirring was continued for 20 minutes before iodoethane (14.5 ml, 28.3 g, 181 mmole, 5 eq) was added dropwise, and the reaction mixture was allowed to stir for an additional 2 hours. The solution was diluted with ether and washed with water. The organic layer was dried (magnesium sulfate), concentrated, and vacuum-dried overnight to yield 17.65 g of crude product as a light yellow oil. This material was triturated with methanol leaving 12.73 g of white solid, melting point 95.5°–97.0° C. Additional product was present in the mother liquor.

(C)
α-Ethyl-[2-(5-chloro-2-aminophenyl)-1-(4-methoxyphenyl)ethyl]propanedioic acid, dimethyl ester α-Ethyl-[2-5-chloro-2-nitrophenyl)-1-(4-methoxyphephenyl) ethyl]propanedioic acid, dimethyl ester (12.64 g, 28.10 mmole) was dissolved in methanol (600 ml) under argon at room temperature. Powdered stannous chloride dihydrate (32.98 g, 146.2 mmole, 5.2 eq) was added followed by concentrated hydrochloric acid (36 ml) with stirring. The solution turned clear and homogenous. After 2 hours, Celite, ethyl acetate and saturated potassium carbonate solution were added with stirring. (The potassium carbonate solution was added portionwise). The suspension was filtered though a pad of Celite and the Celite pad was rinsed with ethyl acetate (3 times). The filtrate was concentrated to remove most of the organic solvents, and the residue was collected by suction-filtration. The crude material was used without further purification.

(D)
6-Chloro-1,3,4,5-tetrahydro-3-ethyl-3-(methoxycarbonyl)-4-(4-methoxyphenyl)-2H-1-benzazepin-2-one α-Ethyl-[2-(5-chloro-2-aminophenyl)-1-(4-methoxyphenyl) ethyl]propanedioic acid, dimethyl ester (9.80 g, 23.3 mmole) and a 25% (by weight) methanol solution of sodium methoxide (24.4 ml, 107 mmole, 4.6 eq, d=0.945) in methanol (148 ml) were refluxed for 28 hours with stirring. The mixture was concentrated, dissolved in ether and washed with water. The aqueous layer was extracted with ether (3 times) and the combined organics were dried (magnesium sulfate) and concentrated. Trituration with ethyl acetate gave pure product (2.71 g), melting point 190°–192° C. Additional product was present in the mother liquor.

(E)
6-Chloro-1,3,4,5-tetrahydro-3-ethyl-4-(4-methoxyphenyl)-2H-1-benzazepin-2-one 6-Chloro-1,3,4,5-tetrahydro-3-ethyl-3-(methoxycarbonyl)-4-(4-methoxyphenyl)-2H-1-benzazepin-2-one (2.67 g, 6.88 mmole) and lithium bromide (3.05 g, 35.1 mmole) in dimethylformamide (40 ml) and water (2 drops) were heated at 130° C. for 4 hours. The cooled mixture was dissolved in ethyl acetate, washed with water, dried (magnesium sulfate), and concentrated. The residue was triturated with hexane to obtain 0.97 g of crude tan solid. Additional product was present in the mother liquor.

(F) (cis)-6-Chloro-1-[2-(dimethylamino)ethyl]-3-ethyl-1,3,4,5-tetrahydro-4-(4-methoxyphenyl)-2H-1-benzazepin-2-one, fumarate (1:1) salt Following the procedure of Example 18D, but omitting the dimethylformamide and using 6-chloro-1,3,4,5-tetrahydro-3-ethyl-4-(4-methoxyphenyl)-2H-1-benzazepin-2-one (920 mg, 2.79 mmole), potassium bicarbonate (1.12 g, 11.2 mmole), methyl ethyl ketone (28 ml), and 2.15 M toluene solution of N,N-dimethyl-2-chloroethylamine (2.6 ml, 5.58 mmole) yielded 1.16 g of crude free amine. An equivalent of fumarate was added to this crude free amine product in methanol, and the mixture was concentrated. The solid was recrystallized (ethyl acetate/hexane, 2 times) giving 560 mg of (cis)-6-chloro-1-[2-(dimethylamino) ethyl]-3-ethyl-1,3,4,5-tetrahydro-4-(4-methoxyphenyl)- 2H-1-benzazepin-2-one, fumarate (1:1) salt in two crops, melting point 179.0°–180.5° C. Additional product was present in the mother liquor.

Analysis Calc'd. for $C_{27}H_{33}N_2O_6Cl \cdot 0.52H_2O$: C, 61.60; H, 6.52; N, 5.32; Cl, 6.73. Found: C, 61.60; H, 6.49; N, 5.20; Cl, 6.52.

Additional compounds falling within the scope of this invention are:

(cis)-7-Chloro-1-[2-(dimethylamino)ethyl]-1,3,4,5-tetrahydro-4-(4-methoxyphenyl)-3-isopropyl-2H-1-benzazepin-2-one (cis)-7-Chloro-1[-2-(dimethylamino)ethyl]-1,3,4,5-tetrahydro-4-(4-methoxyphenyl)-3-butyl-2H-1-benzazepin-2-one (cis)-7-Chloro-1-[2-(dimethylamino)ethyl]-1,3,4,5-tetrahydro-4-(4-methoxyphenyl)-3-isobutyl-2H-1-benzazepin-2-one (cis)-7-Chloro-1-[2-(dimethylamino)ethyl]-1,3,4,5-tetrahydro-4-(4-methoxyphenyl)-3-cyclohexylmethyl-2H-1-benzazepin-2-one (cis)-7-Chloro-1-[2-(dimethylamino)ethyl]-1,3,4,5-tetrahydro-4-(4-methoxyphenyl)-3-cyclopentylmethyl-2H-1-benzazepin-2-one (cis)-7-Chloro-1-[2-(dimethylamino)ethyl]-1,3,4,5-tetrahydro-4-(4-methoxyphenyl)-3-phenylmethyl-2H-1-benzazepin-2-one (cis)-7-Chloro-1-[2-(dimethylamino)ethyl]-1,3,4,5-tetrahydro-4-(4-methoxyphenyl)-3-(2-butenyl)-2H-1-benzazepin-2-one (cis)-7-Chloro-1-[2-(dimethylamino)ethyl]-1,3,4,5-tetrahydro-4-(4-methoxyphenyl)-3-(2-propynyl)-2H-1-benzazepin-2-one (cis)-7-Chloro-1-[2-(dimethylamino)ethyl]-1,3,4,5-tetrahydro-4-(4-methoxyphenyl)-3-[(2-furanyl) methyl]-2H-1-benzazepin-2-one (cis)-7-Chloro-1-[2-(dimethylamino)ethyl]-1,3,4,5-tetrahydro-4-(4-methoxyphenyl)-3-[(2-pyridyl) methyl]-2H-1-benzazepin-2-one (cis)-7-Chloro-1-2-(dimethylamino)ethyl]-1,3,4,5-tetrahydro-4-(4-methoxyphenyl)-3-[(2-pyrrolyl) methyl]-2H-1-benzazepin-2-one (cis)-7-Methoxy-1-[2-(dimethylamino)ethyl]-1,3,4,5-tetrahydro-4-(4-methoxyphenyl)-3-methyl-2H-1-benzazepin-2-one (cis)-6-Methoxy-1-[2-(dimethylamino)ethyl]-1,3,4,5-tetrahydro-4-(4-methoxyphenyl)-3-methyl-2H-1-benzazepin-2-one (cis)-7-(Trifluoromethyl)-1-[2-(dimethylamino) ethyl]-1,3,4,5-tetrahydro-4-(4-methoxyphenyl)-3-isopropyl-2H-1-benzazepin-2-one (cis)-7-(Trifluoromethyl)-1-[2-(dimethylamino) ethyl]-1,3,4,5-tetrahydro-4-(4-methoxyphenyl)-3-ethyl-2H-1-benzazepin-2-one (cis)-6-(Trifluoromethyl)-1-[2-(dimethylamino) ethyl]-1,3,4,5-tetrhydro-4-(4-methoxyphenyl)-b 3-ethyl-2H-1-benzazepin-2-one (cis)-6-(Trifluoromethyl)-1-[2-(methylamino) ethyl]-1,3,4,5-tetrahydro-4-(4-methoxyphenyl)-3-ethyl-2H-1-benzazepin-2-one (cis)-7-(Trifluoromethyl)-1-[2-(dimethylamino) ethyl]-1,3,4,5-tetrahydro-4-(4-methoxyphenyl)-3-(phenylmethyl)-2H-1-benzazepin-2-one (cis)-6-(Trifluoromethyl)-1-[2-(dimethylamino)ethyl]-1,3,4,5-tetrahydro-4-(4-methoxyphenyl)-3-(phenylmethyl)-2H-1-benzazepin-2-one (cis)-6-(Trifluoromethyl)-1-[2-(methylamino)ethyl]-1,3,4,5-tetrahydro-4-(4-methoxyphenyl)-3-(phenylmethyl)-2H-1-benzazepin-2-one (cis)-7-(Trifluoromethyl)-1-[2-(dimethylamino)ethyl]-1,3,4,5-tetrahydro-4-(4-methoxyphenyl)-3-(2-butenyl)-2H-1-benzazepin-2-one (cis)-6-(Trifluoromethyl)-1-[2-(dimethylamino)ethyl]-1,3,4,5-tetrahydro-4-(4-methoxyphenyl)-3-[(2-furanyl)methyl]-2H-1-benzazepin-2-one (cis)-6-(Trifluoromethyl)-1-[2-(dimethylamino)ethyl]-1,3,4,5-tetrahydro-4-(4-methoxyphenyl)-3-(2-propynyl)-2H-1-benzazepin-2-one (cis)-7-(Trifluoromethyl)-1-[2-(dimethylamino)ethyl]-1,3,4,5-tetrahydro-4-(4-methoxyphenyl)-3-(2-propynyl)-2H-1-benzazepin-2-one (cis)-7-Chloro-1-[2-(methylamino)ethyl]-1,3,4,5-tetrahydro-4-(4-methoxyphenyl)-3-allyl-2H-1-benzazepin-2-one

What is claimed is:

1. A compound having the formula

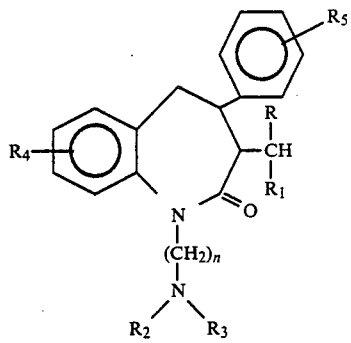

or a pharmaceutically acceptable salt thereof wherein

R and $R_1$ are each hydrogen or alkyl, R is hydrogen and $R_1$ is alkenyl, alkynyl, aryl, heteroaryl or cycloalkyl, or R and $R_1$ together with the carbon atom to which they are attached are cycloalkyl;

$R_2$ and $R_3$ are each independently hydrogen, alkyl, cycloalkyl, or arylalkyl or $R_2$ and $R_3$ together with the nitrogen atom to which they are attached are pyrrolidinyl, piperidinyl, or morpholinyl;

$R_4$ and $R_5$ are each independently hydrogen, halogen, alkyl, alkoxy, aryloxy, arylalkoxy, arylalkyl, hydroxy, alkanoyloxy,

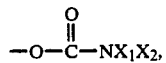

difluoromethoxy, trifluoromethyl, $-NX_3X_4$, $-SO_m$alkyl, or $-SO_m$aryl;

n is 2 or 3;

m is 0, 1 or 2;

$X_1$ and $X_2$ are each independently hydrogen, alkyl, aryl or heteroaryl, or $X_1$ and $X_2$ together with the nitrogen atom to which they are attached are a nitrogen containing heteroaryl;

$X_3$ and $X_4$ are each independently hydrogen, alkyl, alkanoyl, arylcarbonyl, heteroarylcarbonyl, carbamoyl, alkylsulfonyl, or arylsulfonyl; with the proviso that if $R_4$ is a 7-alkyl group, it must have a tertiary carbon atom bonded to the ring;

wherein the term "aryl" refers to phenyl and phenyl substituted with 1, 2 or 3 amino, alkylamino, dialkylamino, nitro, halogen, hydroxyl, trifluoromethyl, alkyl or 1 to 4 carbon atoms, alkoxy of 1 to 4 carbon atoms, alkanoyloxy carbamoyl, or carboxyl groups;

the term "heteroaryl" refers to pyridinyl, pyrrolyl, imidazolyl, furyl, thienyl, or thiazolyl;

the term "nitrogen containing heteroaryl" refers to pyridinyl, pyrrolyl, imidazolyl and thiazolyl;

the terms "alkyl" and "alkoxy" refer to groups having 1 to 10 carbon atoms;

the terms "alkenyl" and "alkynyl" refer to groups having 2 to 10 carbon atoms;

the term "alkanoyl" refers to groups having 2 to 11 carbon atoms; and the term "cycloalkyl" refers to groups having 3, 4 5, 6 or 7 carbon atoms.

2. A compound in accordance with claim 1 wherein $R_2$ and $R_3$ are each independently alkyl or cycloalkyl or $R_2$ and $R_3$ together with the nitrogen atom to which they are attached are pyrrolidinyl, piperidinyl or morpholinyl; and $X_3$ and $X_4$ are each independently hydrogen, alkyl, alkanoyl, arylcarbonyl, heteroarylcarbonyl or carbamoyl.

3. A compound in accordance with claim 1 wherein R and $R_1$ are hydrogen.

4. A compound in accordance with claim 1 wherein R is hydrogen and $R_1$ is alkyl or R and $R_1$ are each alkyl.

5. A compound in accordance with claim 1 wherein R is hydrogen and $R_1$ is alkenyl.

6. A compound in accordnce with claim 5 wherein R is hydrogen and $R_1$ is vinyl.

7. A compound in accordance with claim 1 wherein R is hydrogen and $R_1$ is alkynyl.

8. A compound in accordance with claim 1 wherein R is hydrogen and $R_1$ is aryl.

9. A compound in accordance with claim 1 wherein R is hydrogen and $R_1$ is heteroaryl.

10. A compound in accordance with claim 1 wherein R is hydrogen and $R_1$ is cycloalkyl.

11. A compound in accordance with claim 1 wherein R and $R_1$ together with the carbon atom to which they are attached are cycloalkyl.

12. A compound in accordance with claim 1 wherein at least one of $R_2$ and $R_3$ is hydrogen.

13. A compound in accordance with claim 1 wherein $R_2$ and $R_3$ are each alkyl.

14. A compound in accordance with claim 13 wherein $R_2$ and $R_3$ are each methyl.

15. A compound in accordance with claim 1 wherein $R_2$ and $R_3$ are each cycloalkyl.

16. A compound in accordance with claim 1 wherein $R_2$ and $R_3$ are each arylalkyl.

17. A compound in accordance with claim 1 wherein $R_2$ and $R_3$ together with the nitrogen atom to which they are attached are pyrrolidinyl, piperidinyl or morpholinyl.

18. A compound in accordance with claim 1 wherein $R_4$ is hydrogen.

19. A compound in accordance with claim 1 wherein $R_4$ is halogen or trifluoromethyl.

20. A compound in accordance with claim 19 wherein $R_4$ is chlorine or trifluoromethyl and is located in the 7-position of the benzazepine nucleus.

21. A compound in accordance with claim 1 wherein $R_5$ is alkoxy.

22. A compound in accordance with claim 1 wherein $R_5$ is methoxy and is located in the 4-position of the phenyl ring to which it is attached.

23. A compound in accordance with claim 1 wherein n is 2.

24. A compound in accordance with claim 1 wherein n is 3.

25. The d-cis enantiomer of a compound of claim 1.

26. The compound in accordance with claim 1, (cis)-7-chloro-1-[2-(dimethylamino)ethyl]-1,3,4,5-tetrahydro-4-(4-methoxyphenyl)-3-methyl-2H-1-benzazepin-2-one or a pharmaceutically acceptable salt thereof.

27. The compound in accordance with claim 1, (cis)-7-chloro-1-[2-(dimethylamino)ethyl]-3-ethyl-1,3,4,5-tetrahydro-4-(4-methoxyphenyl)-2H-1-benzazepin-2-one or a pharmaceutically acceptable salt thereof.

28. The compound in accordance with claim 1, (cis)-7-chloro-1-[2-(dimethylamino)ethyl]-1,3,4,5-tetrahydro-4-(4-methoxyphenyl)-3-(2-propenyl)-2H-1-benzazepin-2-one or a pharmaceutically acceptable salt thereof.

29. The compound in accordance with claim 1, (cis)-1-[2-(dimethylamino)ethyl]-1,3,4,5-tetrahydro-4-(4-methoxyphenyl)-3-methyl-7-(trifluoromethyl)-2H-1-benzazepin-2-one or a pharmaceutically acceptable salt thereof.

30. The compound in accordance with claim 1, (cis)-1-[2-(dimethylamino)ethyl]-1,3,4,5-tetrahydro-4-(4-methoxyphenyl)-3-(2-propenyl)-7-trifluoromethyl)-2H-1-benzazepin-2-one or a pharmaceutically acceptable salt thereof.

31. The compound in accordance with claim 1, (cis)-1-[2-(dimethylamino)ethyl]-1,3,4,5-tetrahydro-4-(4-methoxyphenyl)-3-propyl-7-(trifluoromethyl)-2H-1-benzazepin-2-one or a pharmaceutically acceptable salt thereof.

32. The compound in accordance with claim 1, (cis)-1-[2-(dimethylamino)ethyl]-1,3,4,5-tetrahydro-4-(4-methoxyphenyl)-3-(2-propenyl)-6-(trifluoromethyl)-2H-1-benzazepin-2-one or a pharmaceutically acceptable salt thereof.

33. The compound in accordance with claim 1, (cis)-1-[2-(dimethylamino)ethyl]-1,3,4,5-tetrahydro-4-(4-methoxyphenyl)-3-propyl-6-(trifluoromethyl)-2H-1-benzazepin-2-one or a pharmaceutically acceptable salt thereof.

34. The compound in accordance with claim 25, (d-cis)-1-[2-(dimethylamino)ethyl]-1,3,4,5-tetrahydro-4-(4-methoxyphenyl)-3-(2-propenyl)-6-(trifluoromethyl)-2H-1-benzazepin-2-one or a pharmaceutically acceptable salt thereof.

35. The compound in accordance with claim 25, (d-cis)-1-[2-(dimethylamino)ethyl]-1,3,4,5-tetrahydro-4-(4-methoxyphenyl)-3-ethyl-6-(trifluoromethyl)-2H-1-benzazepin-2-one or a pharmaceutically acceptable salt thereof.

36. The compound in accordance with claim 25, (d-cis)-1-[2-(dimethylamino)ethyl]-1,3,4,5-tetrahydro-4-(4-methoxyphenyl)-3-methyl-6-(trifluoromethyl)-2H-1-benzazepin-2-one or a pharmaceutically acceptable salt thereof.

37. The compound in accordance with claim 1, (cis)-1,3,4,5-tetrahydro-4-(4-methoxyphenyl)-3-methyl-1-[2-[methyl(phenylmethyl)amino]ethyl-6-(trifluoromethyl)-2H-1-benzazepin-2-one or a pharmaceutically acceptable salt thereof.

38. The compound in accordance with claim 1, (cis)-1,3,4,5-tetrahydro-4-(4-methoxyphenyl)-3-methyl-1-[2-(methylamino)ethyl]-6-(trifluoromethyl)-2H-1-benzazepin-2-one or a pharmaceutically acceptable salt thereof.

39. The compound in accordance with claim 1, (cis)-1-[2-(diisopropylamino)ethyl]-1,3,4,5-tetrahydro-4-(4- methoxyphenyl)-3-methyl-6-trifluoromethyl)-2H-1-benzazepin-2-one or a pharmaceutically acceptable salt thereof.

40. The d-cis enantiomer of a compound having the formula

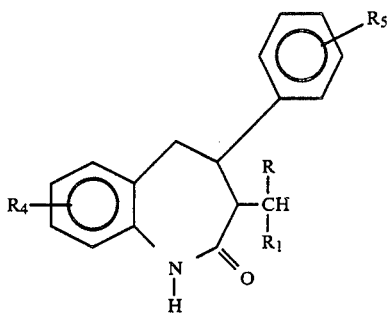

wherein

R and $R_1$ are each hydrogen or alkyl, R is hydrogen and $R_1$ is alkenyl, alkynyl, aryl, heteroaryl or cycloalkyl, or R and $R_1$ together with the carbon atom to which they are attached are cycloalkyl;

$R_4$ and $R_5$ are each independently hydrogen, halogen, alkyl, alkoxy, aryloxy, arylalkoxy, arylakyl, hydroxy, alkanoyloxy,

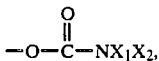

difluoromethoxy, trifluoromethyl, $-NX_3X_4$, $-SO_m$alkyl, or $-SO_m$aryl;

m is 0, 1 or 2;

$X_1$ and $X_2$ are each independently hydrogen, alkyl, aryl or heteroaryl, or $X_1$ and $X_2$ together with the nitrogen atom to which they are attached are a nitrogen containing heteroaryl;

$X_3$ and $X_4$ are each independently hydrogen, alkyl, alkanoyl, arylcarbonyl, heteroarylcarbonyl, carbamoyl, alkylsulfonyl, or arylsulfonyl;

wherein the term "aryl" refers to phenyl and phenyl substituted with 1, 2 or 3 amino, alkylamino, dialkylamino, nitro, halogen, hydroxyl, trifluoromethyl, alkyl of 1 to 4 carbon atoms, alkoxy of 1 to 4 carbon atoms, alkanoyloxy, carbamoyl, or carboxyl groups;

the term "heteroaryl" refers to pyridinyl, pyrrolyl, imidazolyl, furyl, thienyl, or thiazolyl;

the term "nitrogen containing heteroaryl" refers to pyridinyl, pyrrolyl, imidazolyl and thiazolyl;

the terms "alkyl" and "alkoxy" refer to groups having 1 to 10 carbon atoms;

the terms "alkenyl" and "alkynyl" refer to groups having 2 to 10 carbon atoms;

the term "alkanoyl" refers to groups having 2 to 11 carbon atoms; and the term "cycloalkyl" refers to groups having 3, 4, 5, 6 or 7 carbon atoms.

* * * * *